US011430561B2

(12) United States Patent
el Kaliouby et al.

(10) Patent No.: US 11,430,561 B2
(45) Date of Patent: Aug. 30, 2022

(54) REMOTE COMPUTING ANALYSIS FOR COGNITIVE STATE DATA METRICS

(71) Applicant: Affectiva, Inc., Boston, MA (US)

(72) Inventors: Rana el Kaliouby, Milton, MA (US); Rosalind Wright Picard, Newtonville, MA (US); Richard Scott Sadowsky, Sturbridge, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 16/934,069

(22) Filed: Jul. 21, 2020

(65) Prior Publication Data

US 2020/0350057 A1 Nov. 5, 2020

Related U.S. Application Data

(63) Continuation-in-part of application No. 16/781,334, filed on Feb. 4, 2020, which is a continuation-in-part
(Continued)

(51) Int. Cl.
*G06K 9/00* (2022.01)
*G16H 20/70* (2018.01)
(Continued)

(52) U.S. Cl.
CPC ........... *G16H 20/70* (2018.01); *G06K 9/6227* (2013.01); *G06V 40/165* (2022.01);
(Continued)

(58) Field of Classification Search
CPC ........ G16H 20/70; G16H 40/67; G16H 40/63; G06K 9/00248; G06K 9/00288; G06K 9/00302; G06K 9/6227
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Jiang, Ming, and Qi Zhao. "Learning visual attention to identify people with autism spectrum disorder." Proceedings of the ieee international conference on computer vision. 2017. (Year: 2017).*
(Continued)

*Primary Examiner* — Jonathan S Lee
(74) *Attorney, Agent, or Firm* — Adams Intellex, PLC

(57) ABSTRACT

Remote computing analysis for cognitive state data metrics is performed. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. Cognitive state information is generated for each individual, based on the facial expression metric for each individual. The cognitive state information for each individual within the plurality of people who interacted with the rendering is aggregated. The aggregation is based on the facial expression metric for each individual. The cognitive state information that was aggregated is displayed on at least one of the one or more local devices.

25 Claims, 29 Drawing Sheets

Related U.S. Application Data of application No. 16/726,647, filed on Dec. 24, 2019, which is a continuation-in-part of application No. 16/146,194, filed on Sep. 28, 2018, now abandoned, application No. 16/934,069, which is a continuation-in-part of application No. 15/393,458, filed on Dec. 29, 2016, now abandoned, said application No. 16/781,334 is a continuation-in-part of application No. 15/273,765, filed on Sep. 23, 2016, now abandoned, said application No. 15/393,458 is a continuation-in-part of application No. 15/262,197, filed on Sep. 12, 2016, now abandoned, said application No. 16/146,194 is a continuation-in-part of application No. 15/061,385, filed on Mar. 4, 2016, now abandoned, said application No. 15/393,458 is a continuation-in-part of application No. 15/061,385, filed on Mar. 4, 2016, now abandoned, which is a continuation-in-part of application No. 14/848,222, filed on Sep. 8, 2015, now Pat. No. 10,614,289, said application No. 15/262,197 is a continuation-in-part of application No. 14/796,419, filed on Jul. 10, 2015, now abandoned, said application No. 15/273,765 is a continuation-in-part of application No. 14/796,419, filed on Jul. 10, 2015, now abandoned, which is a continuation-in-part of application No. 14/460,915, filed on Aug. 15, 2014, now abandoned, said application No. 14/848,222 is a continuation-in-part of application No. 14/460,915, filed on Aug. 15, 2014, now abandoned, said application No. 15/061,385 is a continuation-in-part of application No. 13/249,317, filed on Sep. 30, 2011, now abandoned, said application No. 14/460,915 is a continuation-in-part of application No. 13/153,745, filed on Jun. 6, 2011, now abandoned.

(60) Provisional application No. 62/955,493, filed on Dec. 31, 2019, provisional application No. 62/954,819, filed on Dec. 30, 2019, provisional application No. 62/954,833, filed on Dec. 30, 2019, provisional application No. 62/926,009, filed on Oct. 25, 2019, provisional application No. 62/925,990, filed on Oct. 25, 2019, provisional application No. 62/893,298, filed on Aug. 29, 2019, provisional application No. 62/827,088, filed on Mar. 31, 2019, provisional application No. 62/679,825, filed on Jun. 3, 2018, provisional application No. 62/637,567, filed on Mar. 2, 2018, provisional application No. 62/625,274, filed on Feb. 1, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.
*G16H 40/67* (2018.01)
*G16H 40/63* (2018.01)
*G06K 9/62* (2022.01)
*G06V 40/16* (2022.01)

(52) U.S. Cl.
CPC .......... *G06V 40/172* (2022.01); *G06V 40/174* (2022.01); *G16H 40/63* (2018.01); *G16H 40/67* (2018.01)

(58) Field of Classification Search
USPC ........................................ 600/407
See application file for complete search history.

(56) References Cited

U.S. PATENT DOCUMENTS

| | | |
|---|---|---|
| 3,870,034 A | 3/1975 | James |
| 4,015,087 A | 3/1977 | Stewart |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |

(56) References Cited

U.S. PATENT DOCUMENTS

| | | |
|---|---|---|
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,046,924 B2 | 5/2006 | Miller et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 10,911,829 B2 * | 2/2021 | el Kaliouby ............ A61B 5/18 |
| 10,950,254 B2 * | 3/2021 | Vaughn ................. G10L 15/22 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0235211 A1 | 10/2005 | Chen |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0167757 A1 | 7/2008 | Kanevsky et al. |
| 2008/0184170 A1 | 7/2008 | Periyalwar |
| 2008/0201144 A1 | 8/2008 | Song et al. |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0175509 A1 | 7/2009 | Gonion et al. |
| 2009/0193344 A1 | 7/2009 | Smyers |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0064040 A1 | 3/2010 | Wise et al. |
| 2010/0070523 A1 | 3/2010 | Delgo et al. |
| 2010/0086215 A1 | 4/2010 | Bartlett et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0007174 A1 | 1/2011 | Bacivarov et al. |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0271484 A1 | 10/2012 | Feit et al. |
| 2012/0324491 A1 | 12/2012 | Bathiche et al. |
| 2013/0023337 A1 | 1/2013 | Bowers et al. |

(56) References Cited

U.S. PATENT DOCUMENTS

| | | |
|---|---|---|
| 2013/0116587 A1 | 5/2013 | Sommo et al. |
| 2013/0197409 A1 | 8/2013 | Baxter et al. |
| 2014/0172910 A1 | 6/2014 | Jung et al. |
| 2016/0063235 A1 | 3/2016 | Tussy |
| 2016/0104486 A1 | 4/2016 | Penilla et al. |
| 2017/0003784 A1 | 1/2017 | Garg et al. |
| 2018/0050696 A1 | 2/2018 | Misu et al. |
| 2018/0251122 A1 | 9/2018 | Golston et al. |
| 2019/0135325 A1 | 5/2019 | Lisseman et al. |
| 2020/0171977 A1 | 6/2020 | Jales Costa et al. |
| 2020/0223362 A1 | 7/2020 | Witte |
| 2020/0285871 A1 | 9/2020 | Tokizaki et al. |
| 2020/0130528 A1 | 10/2020 | Upmanue et al. |

FOREIGN PATENT DOCUMENTS

| | | | |
|---|---|---|---|
| KR | 10-2008-0016303 A | | 2/2008 |
| WO | WO 2011/045422 A1 | | 4/2011 |

OTHER PUBLICATIONS

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

\* cited by examiner

REMOTE COMPUTING ANALYSIS FOR COGNITIVE STATE DATA METRICS

RELATED APPLICATIONS

This application claims the benefit of U.S. provisional patent applications "Vehicle Interior Object Management" Ser. No. 62/893,298, filed Aug. 29, 2019, "Deep Learning In Situ Retraining" Ser. No. 62/925,990, filed Oct. 25, 2019, "Data Versioning for Neural Network Training" Ser. No. 62/926,009, filed Oct. 25, 2019, "Synthetic Data Augmentation for Neural Network Training" Ser. No. 62/954,819, filed Dec. 30, 2019, "Synthetic Data for Neural Network Training Using Vectors" Ser. No. 62/954,833, filed Dec. 30, 2019, and "Autonomous Vehicle Control Using Longitudinal Profile Generation" Ser. No. 62/955,493, filed Dec. 31, 2019.

This application is also a continuation-in-part of U.S. patent application "Robot Navigation for Personal Assistance" Ser. No. 16/781,334, filed Feb. 4, 2020, which claims the benefit of U.S. provisional patent applications "Synthetic Data Augmentation for Neural Network Training" Ser. No. 62/954,819, filed Dec. 30, 2019, "Synthetic Data for Neural Network Training Using Vectors" Ser. No. 62/954,833, filed Dec. 30, 2019, and "Autonomous Vehicle Control Using Longitudinal Profile Generation" Ser. No. 62/955,493, filed Dec. 31, 2019.

The U.S. patent application "Robot Navigation for Personal Assistance" Ser. No. 16/781,334, filed Feb. 4, 2020 is a continuation-in-part of U.S. patent application "Electronic Display Viewing Verification" Ser. No. 16/726,647, filed Dec. 24, 2019, which claims the benefit of U.S. provisional patent applications "Image Analysis for Human Perception Artificial Intelligence" Ser. No. 62/827,088, filed Mar. 31, 2019, "Vehicle Interior Object Management" Ser. No. 62/893,298, filed Aug. 29, 2019, "Deep Learning In Situ Retraining" Ser. No. 62/925,990, filed Oct. 25, 2019, and "Data Versioning for Neural Network Training" Ser. No. 62/926,009, filed Oct. 25, 2019.

The U.S. patent application "Electronic Display Viewing Verification" Ser. No. 16/726,647, filed Dec. 24, 2019, is also a continuation-in-part of U.S. patent application "Facial Tracking With Classifiers For Query Evaluation" Ser. No. 16/146,194, filed Sep. 28, 2018, which claims the benefit of U.S. provisional patent applications "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, "Directed Control Transfer for Autonomous Vehicles" Ser. No. 62/611,780, filed Dec. 29, 2017, "Cognitive State Vehicle Navigation Based on Image Processing" Ser. No. 62/625,274, filed Feb. 1, 2018, "Cognitive State Based Vehicle Manipulation Using Near Infrared Image Processing" Ser. No. 62/637,567, filed Mar. 2, 2018, and "Vehicle Manipulation Using Cognitive State" Ser. No. 62/679,825, filed Jun. 3, 2018.

The U.S. patent application "Facial Tracking With Classifiers For Query Evaluation" Ser. No. 16/146,194, filed Sep. 28, 2018 is also a continuation-in-part of U.S. patent application "Facial Tracking with Classifiers" Ser. No. 14/848,222, filed Sep. 8, 2015 which claims the benefit of U.S. provisional patent applications "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based on Facial Evaluation" Ser. No. 62/128,974, filed Mar. 5, 2015.

The U.S. patent application "Facial Tracking with Classifiers" Ser. No. 14/848,222, filed Sep. 8, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Facial Tracking with Classifiers" Ser. No. 14/848,222, filed Sep. 8, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Facial Tracking With Classifiers For Query Evaluation" Ser. No. 16/146,194, filed Sep. 28, 2018 is also a continuation-in-part of U.S. patent application "Image Analysis for Attendance Query Evaluation" Ser. No. 15/061,385, filed Mar. 4, 2016, which claims the benefit of U.S. provisional patent applications "Viewership Analysis Based on Facial Evaluation" Ser. No. 62/128,974, filed Mar. 5, 2015, "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, and "Analytics for Live Streaming Based on Image Analysis within a Shared Digital Environment" Ser. No. 62/301,558, filed Feb. 29, 2016.

The U.S. patent application "Image Analysis for Attendance Query Evaluation" Ser. No. 15/061,385, filed Mar. 4, 2016 is also a continuation-in-part of U.S. patent application "Facial Tracking with Classifiers" Ser. No. 14/848,222, filed Sep. 8, 2015 which claims the benefit of U.S. provisional patent applications "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Image Analysis for Attendance Query Evaluation" Ser. No. 15/061,385, filed Mar. 4, 2016 is also a continuation-in-part of U.S. patent application "Measuring Affective Data for Web-Enabled Applications" Ser. No. 13/249,317, filed Sep. 30, 2011 which claims the benefit of U.S. provisional patent applications "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Robot Navigation for Personal Assistance" Ser. No. 16/781,334, filed Feb. 4, 2020 is also a continuation-in-part of U.S. patent application "Image Analysis In Support Of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Image Analysis In Support Of Robotic Manipulation" Ser. No. 15/273,765, filed Sep. 23, 2016, is also a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Image Analysis for Data Collected from a Remote Computing Device" Ser. No. 15/393,458, filed Dec. 29, 2016, which claims the benefit of U.S. provisional patent applications "Image Analysis Using Sub-Sectional Component Evaluation to Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Image Analysis for Data Collected from a Remote Computing Device" Ser. No. 15/393,458, filed Dec. 29, 2016 is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Image Analysis for Data Collected from a Remote Computing Device" Ser. No. 15/393,458, filed Dec. 29, 2016 is also a continuation-in-part of U.S. patent application "Image Analysis for Attendance Query Evaluation" Ser. No. 15/061,385, filed Mar. 4, 2016 which claims the benefit of U.S. provisional patent applications "Viewership Analysis Based on Facial Evaluation" Ser. No. 62/128,974, filed Mar. 5, 2015, "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, and "Analytics for Live Streaming Based on Image Analysis within a Shared Digital Environment" Ser. No. 62/301,558, filed Feb. 29, 2016.

The U.S. patent application "Image Analysis for Attendance Query Evaluation" Ser. No. 15/061,385, filed Mar. 4, 2016 is also a continuation-in-part of U.S. patent application "Facial Tracking with Classifiers" Ser. No. 14/848,222, filed Sep. 8, 2015, which claims the benefit of U.S. provisional patent applications "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Facial Tracking with Classifiers" Ser. No. 14/848,222, filed Sep. 8, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Facial Tracking with Classifiers" Ser. No. 14/848,222, filed Sep. 8, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447, 464, filed Feb. 28, 2011, and "Baseline Face Analysis" Ser. No. 61/467,209, filed Mar. 24, 2011.

The U.S. patent application "Image Analysis for Attendance Query Evaluation" Ser. No. 15/061,385, filed Mar. 4, 2016 is also a continuation-in-part of U.S. patent application "Measuring Affective Data for Web-Enabled Applications" Ser. No. 13/249,317, filed Sep. 30, 2011 which claims the benefit of U.S. provisional patent applications "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439, 913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. Each of the foregoing applications is hereby incorporated by reference in its entirety.

FIELD OF INVENTION

This application relates generally to remote computing analysis and more particularly to remote computing analysis for cognitive state data metrics.

BACKGROUND

Social media has taken the world by storm. What arguably began as Morse code messages to distant stations; text based, single computing system message exchange commands; shared dialup bulletin boards and chat rooms; and other modest forums for sharing news, jokes, breadboard computer construction hints and tips, or common interest information; to name only a very few, has evolved into a worldwide phenomenon that includes lavish multimedia systems for exchanging "social media". Social media systems provide seemingly countless opportunities and channels to exchange information with family, friends, colleagues, and the world. Far beyond the mere text and small file exchanges of the past, social media provides high definition video and audio, professionally produced content, fun videos of playful puppies, activity plans for kids' birthday parties, and a dazzling and at times bewildering array of other offerings. While some people still use social media apps and platforms only to keep in touch with classmates, friends, and family, the majority of users also use social media for finding and exchanging political views, coordinating protests or social advocacy events, watching product infomercials, seeking celebrity rumors, or donating to disaster relief aid and fundraising campaigns. With a simple search, one can quickly find affinity groups who share a love of a particular pet breed, a fondness for vacuum tube audio equipment, lost items, wildlife sightings, or nearby pep rallies for political candidates. On the other hand, the searches can also rake up the less pleasant side of social media. Hate speech, trolling, the rantings of political or religious zealots, conspiracy theories, outrageous misstatements or partial truths, and other less than savory content can also be found.

Social media has introduced some unintended societal consequences. Social media use addiction and FOMO or "fear of missing out" has been rampant, particularly among the young. While in general, most people would not say something rude, offensive, derogatory, clearly false, or obviously defamatory directly to someone, there are some who have no hesitation doing exactly that on social media. Much like yelling at another driver from the safety of one's own vehicle, or arguing profanely with a political opponent being interviewed on the radio, posting such material on social media can result in little or no consequence to the poster. With the exceptions of illegal child photographs or other prohibited and banned material, social media posts can persist indefinitely. Another unintended consequence of social media is that the material one posts can be used against her or him in other contexts. Photos of one's youthful hijinks at costume parties decades ago, video of inebriated revelers at a corporate retreat, posting lurid or suggestive photos with a person other than one's spouse or significant other, or reposting of offensive material from a hidden account has caused politicians to resign, job offers to be rescinded, divorce proceedings to be commenced, and employment to be suspended. The usual expectations of privacy and decorous behavior that exist offline do not always extend to the online realm of social media.

SUMMARY

Remote computing analysis for cognitive state data metrics is performed. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. Cognitive state information is generated for each individual, based on the facial expression metric for each individual. The cognitive state information for each individual within the plurality of people who interacted with the rendering is aggregated. The aggregation is based on the facial expression metric for each individual. The cognitive state information that was aggregated is displayed on at least one of the one or more local devices.

Analysis of people, as they interact with the internet, can be performed by gathering cognitive states through evaluation of facial expressions, head gestures, and physiological conditions. This analysis can be connected to specific interactions with web pages or portions of a given web page. The aggregated cognitive state information can include norms derived from the plurality of people. The norms can be based on contextual information. The method can further comprise associating the aggregated cognitive state information with the rendering. The method can further comprise inferring of cognitive states based on the cognitive state data collected from the plurality of people. The rendering can be one of a group comprising a button, an advertisement, a banner ad, a drop-down menu, and a data element on a web-enabled application. The rendering can be one of a group comprising a landing page, a checkout page, a webpage, a website, a web-enabled application, a video on a web-enabled application, a game on a web-enabled application, and a virtual world. The collecting cognitive state data can involve capturing of one of a group comprising physiological data and facial data. A webcam can be used to capture one or more of the facial data and the physiological data. The physiological data can be used to determine autonomic activity. The autonomic activity can be one of a group comprising heart rate, respiration, and heart rate variability. The facial data can include information on one or more of a group comprising facial expressions, action units, head gestures, smiles, brow furrows, squints, lowered eyebrows, raised eyebrows, and attention. The method can further comprise tracking of eyes to identify the rendering with which interacting is accomplished. The tracking of eyes can identify a portion of the rendering on which the eyes are focused. A webcam can be used to track the eyes. The method can further comprise recording of eye dwell-time on the rendering and associating information on the eye dwell-time to the rendering and to the cognitive states. The interacting can include one of a group comprising viewing, clicking, and mousing over. The method can further comprise opting in, by an individual from the plurality of people, to allowing facial information to be aggregated. The method can further comprise opting in, by an individual from the plurality of people, to allowing uploading of information to the server.

Aggregation of the aggregated cognitive state information can be accomplished using computational aggregation. In some embodiments, aggregation of the aggregated cognitive state information is performed on a demographic basis so that cognitive state information is grouped based on the demographic basis. The method can further comprise creating a visual representation of one or more of the aggregated cognitive state information and cognitive state information on an individual from the plurality of people. The visual representation can display the aggregated cognitive state information on a demographic basis. The method can further comprise animating an avatar to represent one or more of the aggregated cognitive state information and cognitive state information on an individual from the plurality of people. The method can further comprise synchronizing the aggregated cognitive state information with the rendering. The method can further comprise capturing contextual information about the rendering. The contextual information can include one or more of a timeline, a progression of webpages, or an actigraph. The cognitive states can include one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, fatigue, drowsiness, or mirth.

A computer-implemented method for analysis is disclosed comprising: collecting cognitive state data from a plurality of people as they interact with a rendering, wherein the cognitive state data includes video facial data, collected on one or more local devices, from the plurality of people; uploading information to a remote server, wherein the information includes the cognitive state data; calculating a facial expression metric, based on a plurality of image classifiers, for each individual within the plurality of people; generating cognitive state information for each individual, based on the facial expression metric for each individual; aggregating the cognitive state information for each individual within the plurality of people who interacted with the rendering, based on the facial expression metric for each individual; and displaying, with the rendering, the cognitive state information that was aggregated, on at least one of the one or more local devices.

In embodiments, the cognitive state information can include a cognitive state metric. In embodiments, the aggregated cognitive state information can include aggregated cognitive state metrics. Some embodiments can include deriving norms for the plurality of people. In embodiments, the norms for the plurality of people can be based on the aggregated cognitive state information and the norms for the plurality of people can be based on contextual information. And in some embodiments, the norms can be derived based on cognitive state event temporal signatures. Some embodiments include aggregating two or more cognitive state metrics for the individual with two or more cognitive state metrics for an additional individual within the plurality of people. And some embodiments base further aggregation on a comparison of matched cognitive state metrics for the individual and the additional individual. In some embodiments, the cognitive state data includes audio data, such as ambient sounds, speech vocalizations, and non-speech vocalizations.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

The present disclosure provides a description of various methods and systems for remote computing analysis for cognitive state data metrics, which can include analyzing people's cognitive states as they interact with websites and other features on the internet. A cognitive state can be an emotional state or a cognitive state. Examples of emotional states include happiness or sadness, and examples of cognitive states include concentration or confusion. Observing, capturing, and analyzing these cognitive states can yield significant information about people's reactions to websites that far exceed current capabilities in website analytics.

A challenge solved by this disclosure is the analysis of cognitive states within a web-oriented environment using remote computing. Information on cognitive states can be collected on a client machine and either uploaded to a server in a raw format or analyzed and abstracted, then uploaded. The server, which can comprise a cloud-based system, a datacenter system, a dedicated system, and so on, can perform analysis on the cognitive states as an individual or group of individuals interacts with videos, advertisements, webpages, and the like based on the cognitive state information which was uploaded. The cognitive state information can be aggregated across a group of people to provide summaries on people's cognitive states as they interact with web-enabled applications. The aggregated information can provide normative criteria that are important for comparing customer experiences across different applications and across common experiences within many applications, such as online payment or point of sale. The applications can be webpages, websites, web portals, mobile device applications, dedicated applications, and similar web-oriented tools and capabilities. The aggregated cognitive state information can be downloaded to the original client machine from which the cognitive state information was uploaded, or alternately can be downloaded to another client machine for presentation. Cognitive states, which have been inferred based on the cognitive state information, can then be presented on a client machine display along with a rendering showing the material with which people interacted. Emotional state, mental state, cognitive state, and so on, are terms of art which may connote slight differences of emphasis, for example an emotional state of "happiness" vs. a cognitive state of "distractedness," but at a high level, the terms can be used interchangeably. In fact, because the human mind of an individual is often difficult to understand, even for the individual, emotional, mental, and cognitive states may easily be overlapping and appropriately used in a general sense.

Figure 1:
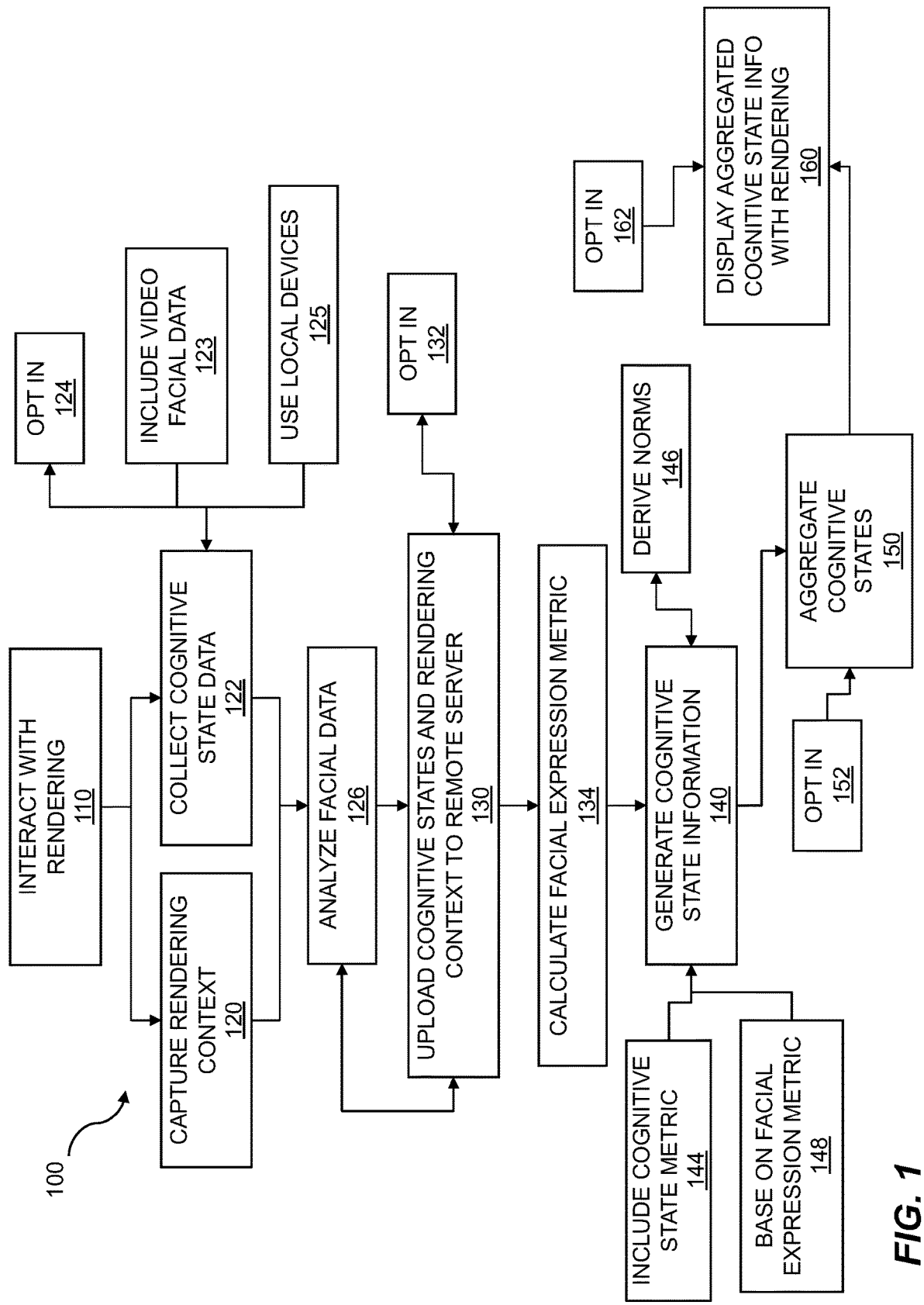
FIG. 1 is a flow diagram for providing remote computing analysis for cognitive state metrics.

FIG. 1 is a flow diagram for providing remote computing analysis for cognitive state metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. The process can include a method for analyzing web-enabled application traffic. The flow 100 begins with a person or persons interacting with a rendering 110. The process can include interacting with a rendering by a plurality of people. A rendering can include a landing page, a checkout page, a webpage, a website, a web-enabled application, a social media post, a video on a web-enabled application, a game on a web-enabled application, a virtual world, or other visible outputs of various web-enabled applications. A rendering can also include, among other items, a portion of one of items such as a button, an advertisement, a banner ad, a drop-down menu, a section of text, an image, and a data element on a web-enabled application. The interacting with the rendering can include a variety of types of interaction, including viewing, clicking, typing, filling in form data, mousing over the rendering, or any type of human-machine interaction. The flow 100 can continue with capturing contextual information about the rendering 120. The context can be any information related to the rendering, such as a timeline, a progression of web pages, an actigraph, demographic information about the individual interacting with the rendering, or any other type of information related to the rendering, the individual, or the circumstances of the interaction. The timeline can include information on when a rendering was interacted with or viewed. For instance, a video can be viewed, and the times when cognitive states were collected along with the corresponding time points in the video can be recorded. In some embodiments, the contextual information includes a progression of web pages. A progression of web pages can include the uniform resource locators (URLs) viewed and the order in which they were recorded. By collecting a progression of web pages, collected cognitive states can be correlated with the web pages viewed.

The flow 100 continues with collecting cognitive state data 122 from a plurality of people as they interact with a rendering. Cognitive state data that can be collected includes physiological data, facial data, other images, sounds, timelines of user activity, or any other information gathered about an individual's interaction with the rendering. Cognitive state data can include video facial data 123 collected by a device local to the person or persons 125 on whom the video facial data is being collected, such as a camera included with a smartphone or a webcam included with or added on to a laptop or other personal computer. The data can be collected by a camera in a vehicle. Thus, the collecting cognitive state data involves capturing of one of a group comprising physiological data and facial data, in some embodiments. Cognitive state information can include the cognitive state data and any type of inferred information about the individuals including, but not limited to, frustration, confusion, disappointment, hesitation, cognitive overload, focusing, being engaged, attending, boredom, exploration, confidence, trust, delight, or satisfaction. An example of a rendering can be a checkout page on a website. If the total bill or the means of shipping is not clear, an individual can exhibit a cognitive state of confusion or uncertainty. In another example, a rendering can be a video trailer for a movie that will soon be released. An individual can find the plot line and action engaging, thereby exhibiting corresponding cognitive states such as attention and engagement, which can be collected along with and/or inferred from the cognitive state data.

An individual can opt in 124 to the collection of cognitive states or cognitive state data either before or after data is collected. In one embodiment, an individual is asked permission to collect cognitive states prior to viewing or interacting with a rendering. In another embodiment, an individual is asked permission to collect cognitive states after the rendering is interacted with or viewed. In this case, any information collected on cognitive states would be discarded if permission were not granted. In another embodiment, an individual is asked a general question about permission for collecting of cognitive states prior to viewing or interacting with a rendering, and then a confirmation permission is requested after the rendering is interacted with or viewed. The intent of these opting-in permission requests would be to give the individual control over whether cognitive state data and/or cognitive state information were collected and, further, what type of information can be used. In some embodiments, however, no opt-in permission is obtained, or the opt-in can be implicit due to the circumstances of the interaction. The flow 100 includes analyzing the facial data 126, wherein the analyzing is based on a plurality of image classifiers. In embodiments, the analyzing includes using an image classifier from the plurality of image classifiers to detect one or more faces in the facial data. In some embodiments, the analyzing further includes using an image classifier from the plurality of image classifiers to detect facial features or facial landmarks in the facial data.

The cognitive states and rendering context can be uploaded to a remote server 130. The process thus can include uploading information to a server, based on the cognitive state data, from the plurality of people who interact with the rendering. The uploading can only be for the actual data collected, and/or the uploading can be for inferred cognitive states. The collection of cognitive states 122 and capturing of rendering context 120 can be performed locally on a local device such as a client computer. Alternatively, the physiological and/or facial data can be captured locally and uploaded to a server where further analysis is performed to infer the cognitive states. An individual can opt in 132 for allowing the uploading of information to the server. Thus, the process can include opting in, by an individual from the plurality of people, to allowing uploading of cognitive state data to the server. The information can also include context; thus, the process can also include opting in, by an individual from the plurality of people, to allowing the uploading of information to the server. In some embodiments, the collected cognitive states are displayed to the individual prior to uploading of information. The individual can then be asked permission to upload the information. In some embodiments, an individual provides further permission after uploading or is asked to confirm that the uploading which was performed is still acceptable. If permission is not granted during this opt-in 132 phase, then the information would be deleted from the server and not used any further. The flow 100 includes calculating a facial expression metric 134 based on a plurality of image classifiers for each individual within the plurality of people. In embodiments, multiple facial expression metrics have been obtained from previous analyses of numerous people.

The flow 100 can include generating cognitive state information 140 for each individual within the plurality of people. The cognitive state information can be based on the facial expression metric 148, or metrics, that were calculated, along with any of the cognitive state data that was collected. The cognitive state information can include cognitive states inferred from the cognitive state data and/or the facial expression metric. The cognitive state information can be generated by using classifiers on a neural network being executed on the remote server. Cognitive states can include one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, mirth, and so on. The identifying cognitive state data, the calculating one or more facial expression metrics, and the generating one or more cognitive states can be accomplished using classifiers operating within a neural network. The cognitive state information can include a cognitive state metric 144 that provides a quantitative measurement of cognitive states. The cognitive state information can be used to derive norms 146 for an individual, an aggregation of individuals, a plurality of people, a demographically segregated subset of a plurality of people, and so on, and/or it can be related to the rendering or the rendering context.

Cognitive states can be aggregated 150 between multiple individuals. A single rendering can be interacted with or viewed by numerous people. The cognitive states can be collected for these people and then aggregated together so that an overall reaction by the people can be determined. The aggregation can occur in the same system/process or a different system/process than the system/process used to collect cognitive state, or alternatively, the aggregation can occur on a server. The aggregated information on the cognitive states can then be sent between systems or between processes on the same system. Thus, the process can include receiving aggregated cognitive state information on the plurality of people who interact with the rendering. In some embodiments, the aggregated cognitive state information is based on the comparing of the plurality of cognitive state event temporal signatures. The comparing of the plurality of cognitive state event temporal signatures against the information that was uploaded can result in identification of a particular cognitive state. This cognitive state would correspond to an occurrence of a facial expression or series of expressions which match the particular cognitive state event temporal signature. A plurality of people can have common or similar facial expressions, or series of expressions, and these expressions can match the particular cognitive state event temporal signature. Individuals can opt in to having their cognitive state information aggregated with others. In some embodiments, an individual grants permission for their cognitive states to be aggregated or otherwise used in analysis. Thus, the process can include opting in 152, by an individual from the plurality of people, to allowing information on the face to be aggregated. This information can include all facial data or can include only part of the information. For instance, some individuals can choose to have video of their faces excluded, but can choose to have other information on facial action units, head gestures, and the like included. In some embodiments, the aggregating is accomplished using computational aggregation. In some embodiments, analysis is integrated over several web pages, over multiple renderings, or over a period of time. For example, a checkout experience can include four web pages and the objective is to capture the reaction to this group of four web pages. Thus, the analysis can include integrating the inferred cognitive states for the four pages for an individual. Further, the inferred cognitive states for these four pages can be aggregated and thereby combined for the multiple individuals.

The flow 100 can continue with displaying the aggregated cognitive states with the rendering 160. Thus, the process can include displaying the aggregated cognitive state information with the rendering. The information associated can include facial video, other facial data, physiological data, and inferred cognitive states. In some embodiments, the cognitive states are synchronized with the rendering using a timeline, webpage sequence order, or another rendering context. The process can therefore continue with associating the aggregated cognitive state information with the rendering. The displaying can be enabled by an opting-in 162 of an individual. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors. Various embodiments of the flow 100, or portions thereof, can be included on a semiconductor chip and implemented in special purpose logic, programmable logic, and so on. Various embodiments of flow 100, or portions thereof, can be used for remote computing analysis for cognitive state data metrics.

Figure 2:
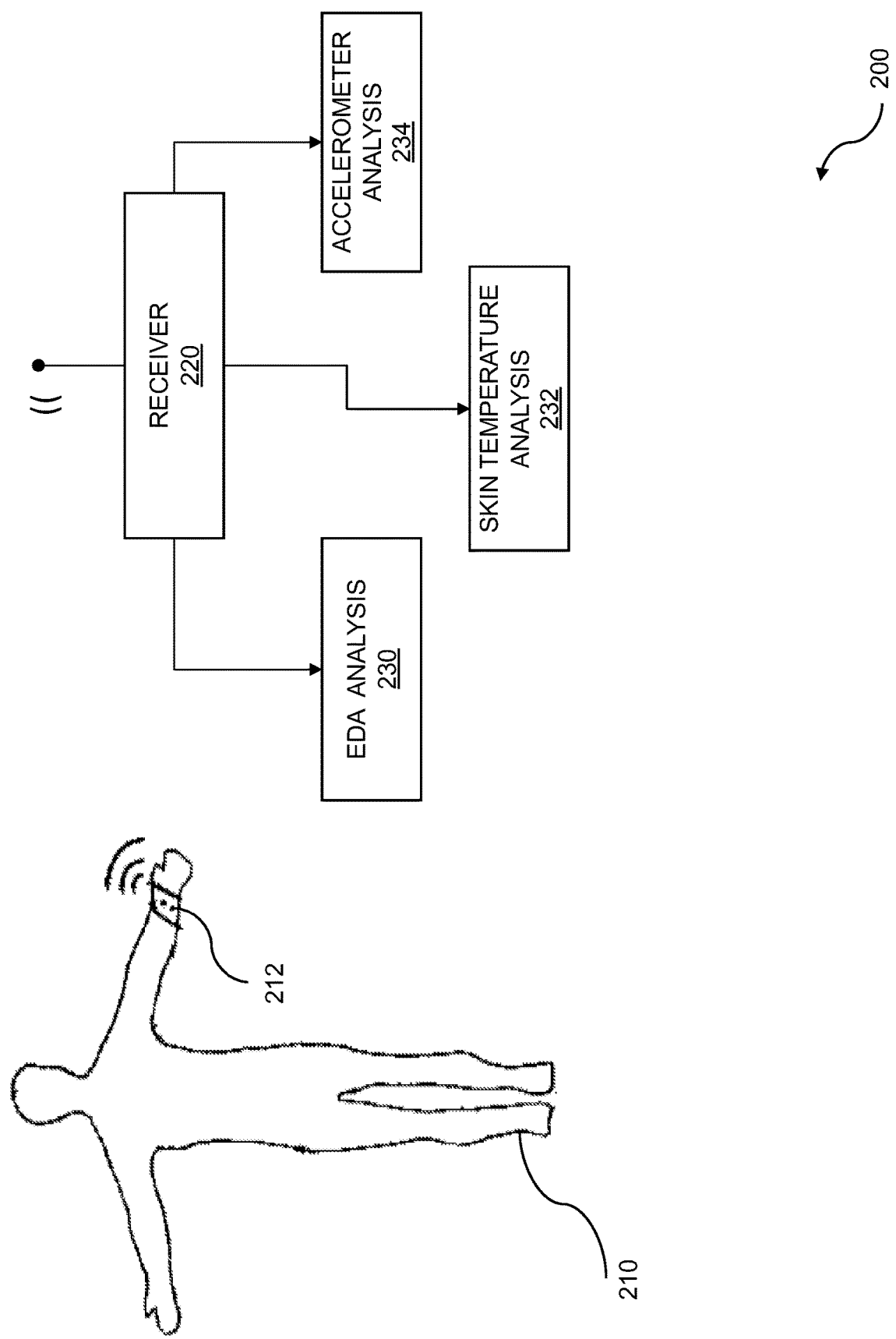
FIG. 2 is a diagram representing physiological analysis.

FIG. 2 is a diagram representing physiological analysis. Physiological analysis can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. A system 200 can analyze a person 210 from whom data is being collected. The person 210 can have a sensor 212 attached to him or her. The sensor 212 can be placed on the wrist, palm, hand, head, or another part of the body. The sensor 212 can include detectors for physiological data, such as electrodermal activity, skin temperature, accelerometer readings, and the like. Other detectors for physiological data, such as heart rate, blood pressure, EKG, EEG, further brain waves, and other physiological detectors can be included as well. The sensor 212 can transmit information collected to a receiver 220 using wireless technology such as Wi-Fi, Bluetooth, 802.11, cellular, or other bands. In other embodiments, the sensor 212 communicates with the receiver 220 by other methods such as a wired interface, or an optical interface. The receiver can provide the data to one or more components in the system 200. In some embodiments, the sensor 212 records various physiological information in memory for later download and analysis. In some embodiments, the download of data which includes the recorded physiological information is accomplished through a USB port or another wired or wireless connection.

Cognitive states can be inferred based on physiological data, such as physiological data from the sensor, or inferred based on facial expressions and head gestures observed by a webcam. The cognitive states can be analyzed based on arousal and valence. Arousal can range from being highly activated, such as when someone is agitated, to being entirely passive, such as when someone is bored. Valence can range from being very positive, such as when someone is happy, to being very negative, such when someone is angry. Physiological data can include electrodermal activity (EDA) or skin conductance or galvanic skin response (GSR), accelerometer readings, skin temperature, heart rate, heart rate variability, and other types of analysis of a human being. In embodiments, a webcam is used to capture the physiological data. It will be understood that both here and elsewhere in this document, physiological information can be obtained either by sensor or by facial observation. Facial data can include facial actions and head gestures used to infer cognitive states. Further, the data can include information on hand gestures or body language and body movements such as visible fidgets. In some embodiments, these movements are captured by cameras or by sensor readings. Facial data can include tilting the head to the side, leaning forward, smiling, frowning, as well as many other gestures or expressions.

In some embodiments, electrodermal activity is collected continuously, every second, four times per second, eight times per second, 32 times per second, or on some other periodic basis. The electrodermal activity can be recorded. The activity can be recorded to a disk, to a tape, onto flash memory, into a computer system, or it can be streamed to a server. The electrodermal activity can be analyzed 230 to indicate arousal, excitement, boredom, or other cognitive states based on changes in skin conductance. Skin temperature can be collected on a periodic basis and can be recorded. The skin temperature can be analyzed 232 and can indicate arousal, excitement, boredom, or other cognitive states based on changes in skin temperature. Accelerometer data can be collected and indicate one, two, or three dimensions of motion. The accelerometer data can be recorded. The accelerometer data can be analyzed 234 and can indicate a sleep pattern, a state of high activity, a state of lethargy, or another state based on accelerometer data. The various data collected by the sensor 212 can be used along with the facial data captured by the webcam. Thus, in some embodiments, cognitive state data is collected by the capturing of one of a group comprising physiological data and facial data.

Figure 3:
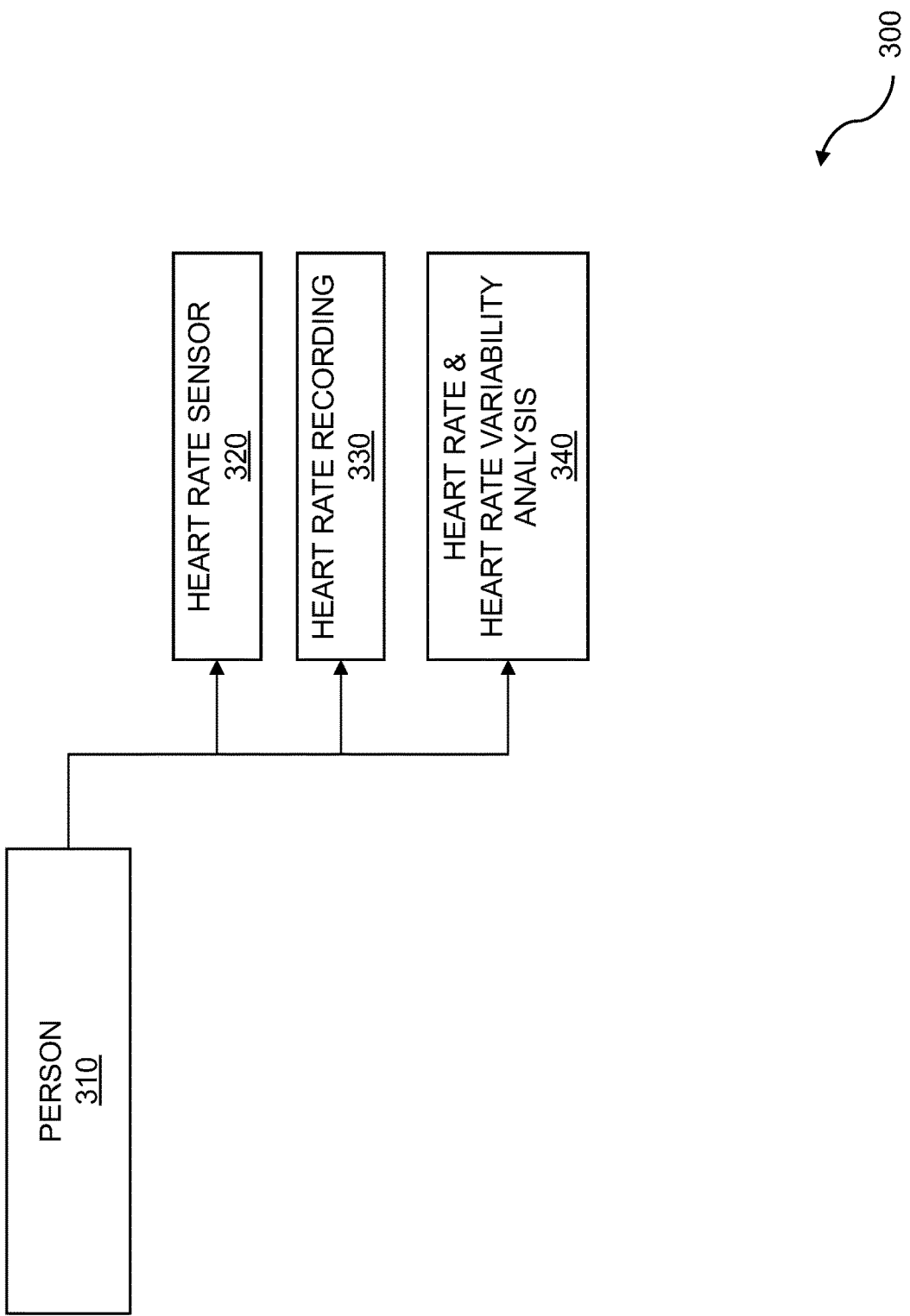
FIG. 3 is a diagram of heart related sensing.

FIG. 3 is a diagram of heart related sensing. Heart related sensing can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. A person 310 is observed by a system 300 which can include a heart rate sensor 320. The observation can be performed through a contact sensor or through video analysis, which enables capture of heart rate information, or through another form of contactless sensing. In some embodiments, a webcam is used to capture the physiological data. In some embodiments, the physiological data is used to determine autonomic activity, and the autonomic activity is one of a group comprising heart rate, respiration, and heart rate variability. Other embodiments determine other autonomic activity such as pupil dilation or other autonomic activities. The heart rate can be recorded 330 to a disk, to a tape, into flash memory, into a computer system, or it can be streamed to a server. The heart rate and heart rate variability can be analyzed 340. An elevated heart rate can indicate excitement, nervousness, or other cognitive states. A lowered heart rate can indicate calmness, boredom, or other cognitive states. The level of heart-rate variability can be associated with fitness, calmness, stress, and age. The heart-rate variability can be used to help infer the cognitive state. High heart-rate variability can indicate good health and lack of stress. Low heart-rate variability can indicate an elevated level of stress.

Figure 4:
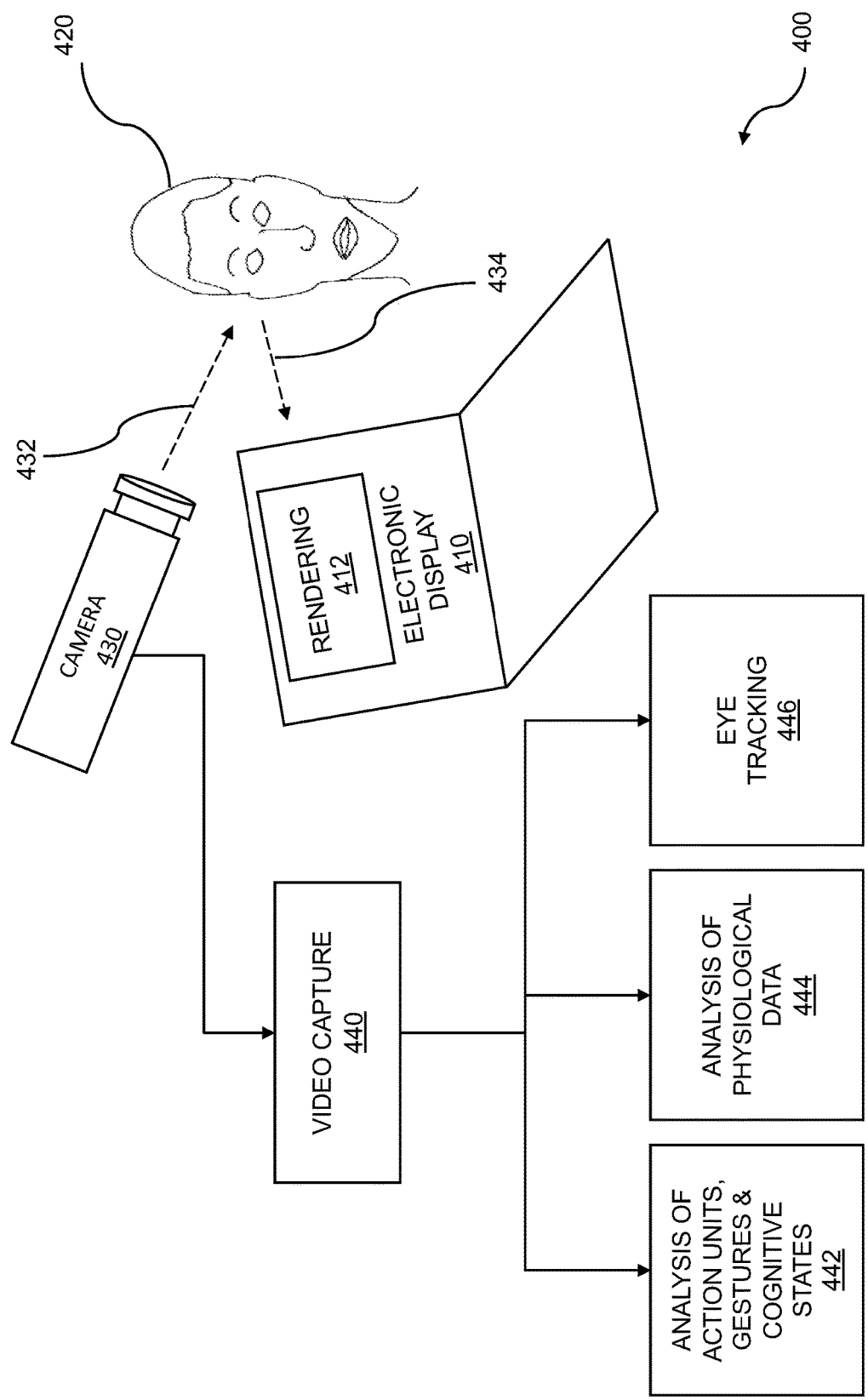
FIG. 4 is a diagram for capturing facial response to a rendering.

FIG. 4 is a diagram for capturing facial response to a rendering. The system 400 can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. In the system 400, an electronic display 410 can show a rendering 412 to a person 420 in order to collect facial data and/or other indications of cognitive state. A webcam 430 is used to capture the facial data in some embodiments, although in other embodiments, the webcam 430 is used to capture one or more of the facial data and the physiological data. The facial data includes information on one or more of a group comprising facial expressions, action units, head gestures, smiles, brow furrows, squints, lowered eyebrows, raised eyebrows, and attention, in various embodiments. The webcam 430 can capture video, audio, and/or still images of the person 420. A webcam, as the term is used herein, can be a video camera, still camera, thermal imager, CCD device, phone camera, three-dimensional camera, a depth camera, multiple webcams used to show different views of the person, or any other type of image capture apparatus that can allow captured data to be used in an electronic system. The electronic display 410 can be a computer display, a laptop screen, a mobile device display, a cell phone display, or some other electronic display. The rendering 412 can be a landing page, a checkout page, a webpage, a website, a web-enabled application, a video on a web-enabled application, a game on a web-enabled application, a virtual world, or some other output of a web-enabled application. The rendering 412 can also be a portion of what is displayed, such as a button, an advertisement, a banner ad, a dropdown menu, and a data element on a web-enabled application or other portion of the display. In some embodiments, the webcam 430 observes 432 the eyes of the person. For the purposes of this disclosure, the word "eyes" can refer to either one or both eyes of an individual, or to any combination of one or both eyes of individuals in a group. The eyes can move as the rendering 412 is observed 434 by the person 420. The images of the person 420 from the webcam 430 can be captured by a video capture unit 440. In some embodiments, video is captured, while in others, a series of still images is captured. The captured video or still images can be used in one or more pieces of analysis.

Analysis of action units, gestures, and cognitive states 442 can be accomplished using the captured images of the person 420. The action units can be used to identify smiles, frowns, and other facial indicators of cognitive states. The gestures, including head gestures, can indicate interest or curiosity. For example, a head gesture of moving toward the electronic display 410 can indicate increased interest or a desire for clarification. Based on the captured images, analysis of physiological data 444 can be performed. Respiration, heart rate, heart rate variability, perspiration, temperature, and other physiological indicators of cognitive state can be observed by analyzing the images. Therefore, in various embodiments, a webcam is used to capture one or more of the facial data and the physiological data.

In some embodiments, a webcam is used to track the eyes. Tracking of eyes 446 to identify the rendering with which interacting is accomplished can be performed. In some embodiments, the tracking of the eyes identifies a portion of the rendering on which the eyes are focused. Thus, various embodiments perform tracking of eyes to identify one of the rendering and a portion of the rendering, by which interacting is accomplished. In this manner, by tracking of eyes, cognitive states can be associated with a specific rendering or portion of the rendering. For example, if a button on a webpage is unclear as to its function, a person can indicate confusion. By tracking of eyes, it will be clear that the confusion is over the button in question, rather than some other portion of the web page. Likewise, if a banner ad is present, by tracking of eyes, the portion of the banner ad which exhibits the highest arousal and positive valence can be determined. Further, in some embodiments, the process includes recording of eye dwell-time on the rendering and associating information on the eye dwell-time to the rendering and to the cognitive states. The eye dwell-time can be used to augment the cognitive state information to indicate the level of interest in certain renderings or portion of renderings.

Figure 5:
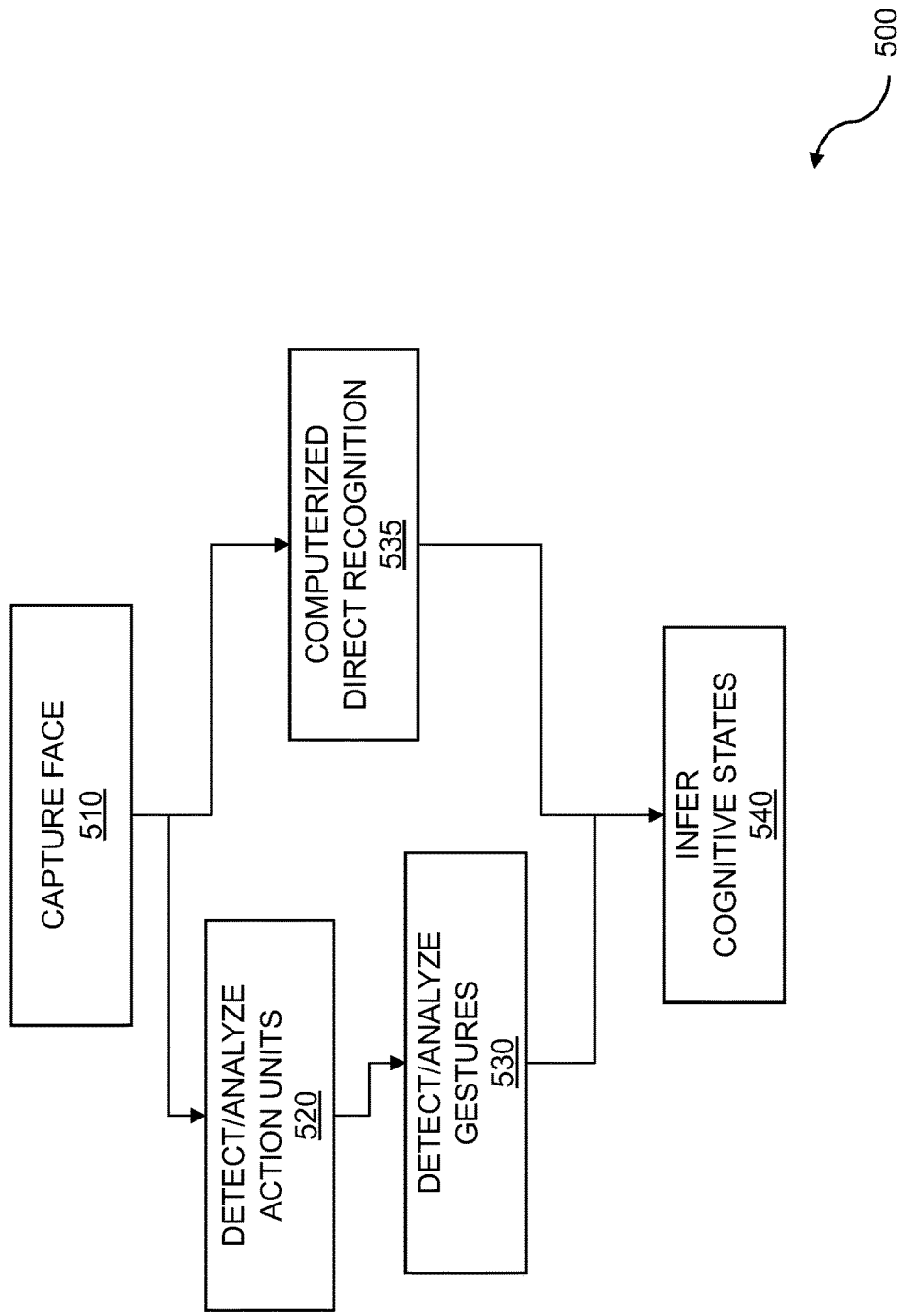
FIG. 5 is a flowchart for performing facial analysis.

FIG. 5 is a flowchart for performing facial analysis. The flow 500 can enable remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. The flow 500 begins by capturing the face 510 of a person. The capture can be accomplished by video or by a series of still images. The flow 500 can include detection and analysis of action units 520. The action units can include the raising of an eyebrow, raising of both eyebrows, a twitch of a smile, a furrowing of the eye brows, a flaring of nostrils, a squinting of the eyes, and many other possibilities. These action units can be automatically detected by a computer system analyzing the video. Alternatively, a combination of automatic detection by a computer system and human input can be provided to enhance the detection of the action units. The flow 500 can include detection and analysis of head and facial gestures 530. Gestures can include tilting the head to the side, leaning forward, smiling, frowning, as well as many other gestures.

In other embodiments, computerized direct recognition 535 of facial expressions and head gestures or cognitive states is performed. When direct recognition is performed, feature recognition and classification can be included in the process. An analysis to infer cognitive states 540 can be performed. The cognitive states can include frustration, confusion, disappointment, hesitation, cognitive overload, focusing, being engaged, attending, boredom, exploration, confidence, trust, delight, and satisfaction, as well many others.

Figure 6:
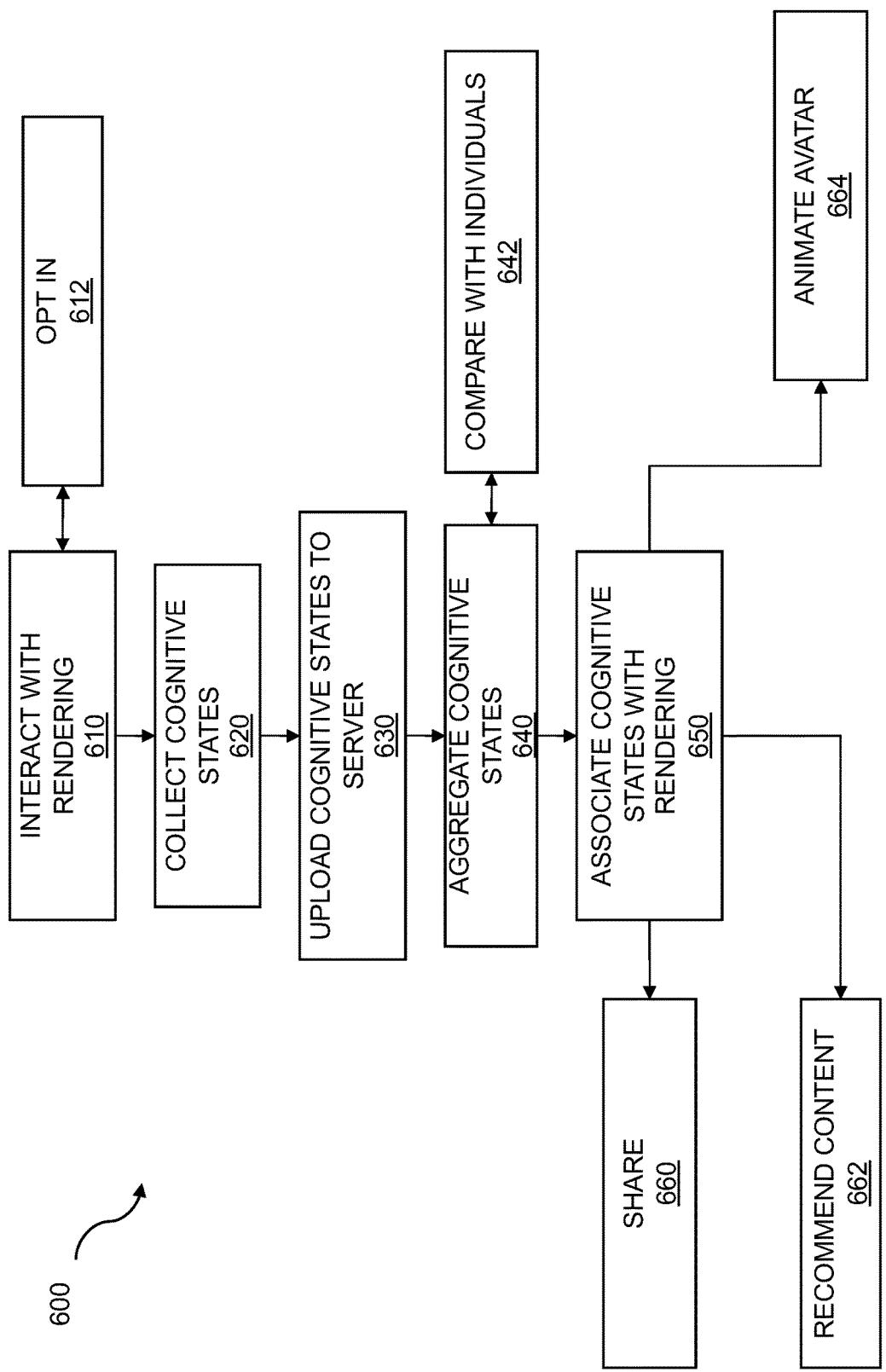
FIG. 6 is a flowchart for using cognitive state information.

FIG. 6 is a flowchart for using cognitive state information. The flow 600 can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. The flow 600 begins with an individual interacting with a rendering 610, such as, for example, a website. The interacting can include viewing, clicking on, or performing any other web-enabled application-oriented activity. The individual can opt in 612 to having information related to cognitive states collected, uploaded, aggregated, and/or shared, including opting in to allowing information on the face to be aggregated. The cognitive states can be collected 620 as the rendering is interacted with or viewed. The cognitive states can be inferred based on the facial and physiological data which is collected. The cognitive states can be inferred based on computer-based analysis on a client device. Some embodiments are configured for receiving cognitive state data collected from a plurality of people as they interact with a rendering, as the collecting can be done on a different system. The cognitive states can be uploaded to a server 630. The cognitive states can be inferred based on computer-based analysis on a server device. Further, cognitive state analysis can be aided by human interaction.

The cognitive states can be aggregated 640 with other people's cognitive state information which was collected. In some embodiments, aggregating cognitive state information on the plurality of people who interact with the rendering is accomplished. Receiving aggregated cognitive state information, based on the cognitive state data from the plurality of people who interact with the rendering, is accomplished in other embodiments, where the aggregating is done on a different system. Each of the people can have interacted with or viewed the same rendering. The cognitive states are collected and synchronized with information about the rendering. The synchronization can be based on a timeline, a sequence of web pages viewed, an eye tracking of a rendering or portion of a rendering, or some other synchronization technique. The aggregation can be accomplished by means of the scaling of collected information. The aggregation can be achieved by the combining of the various cognitive states that were inferred. The aggregation can be a combination of electrodermal activity, heart rate, heart rate variability, respiration, or some other physiological reading. The aggregation can involve computational aggregation. In some embodiments, aggregation involves noise cleaning of the data through techniques involving a low pass and/or a high pass filter or a band pass filter on the data. Normalization can occur to remove any noise spikes on the data. Noise spikes are frequently removed through nonlinear filtering, such as robust statistics or morphological filters. Time shifts can occur to put the data collected on the same effective timeline. In some embodiments, this time shifting is referred to as time warping. Normalization and time warping can be interchanged in order. The collected data can be averaged. Robust statistics such as median values can be obtained. Using these techniques, outliers are removed and data below a certain threshold is discarded. Finally, visualization and display can be performed on the data. For example, electrodermal activity measurements can be aggregated using the techniques described above so that a quantitative set of numbers representing a group of people's responses can be determined. Additionally, in some embodiments, non-linear stretching is used to focus on a small range of information. For example, a specific time range can be of particular interest due to the cognitive state response. Therefore, the time before and after this time can be compressed, while the time range of interest is expanded. In some embodiments, the aggregated cognitive state information includes norms derived from the plurality of people. The norms can be based on contextual information, where the contextual information can be based on information from the rendering, information from sensors, or the like. In embodiments, norms are derived based on the cognitive state event temporal signatures. In embodiments, the flow 600 further comprises collecting further cognitive state data from a first individual and comparing the further cognitive state data from the first individual 642 with the aggregated cognitive state information. The collecting of the further cognitive state data can be accomplished by video collection of facial data. The comparing can be used to identify common characteristics or differences between the individual and a population of people. In some embodiments, the flow 600 further comprises collecting additional further cognitive state data from a second individual and comparing the additional further cognitive state data from the second individual with the aggregated cognitive state information. The comparing can also identify differences between the first and the second individuals. In embodiments, the first individual and the second individual are part of the plurality of people. In other embodiments, the first individual and the second individuals are part of a different population and the comparing is used to target various products or services provided through a web-enabled application.

The flow 600 continues by associating the aggregated cognitive state information with the rendering 650. The rendering, such as a web page, video, or some other web-enabled application, can have aggregated cognitive states associated with the rendering. In this manner, a web page button can be associated with confusion, a video trailer can be associated with anticipation, or a checkout page or pages can be associated with confidence. Likewise, certain times in a video can be associated with positive cognitive states, while other times in a video can be associated with negative cognitive states.

The cognitive states can be shared 660. The aggregated cognitive state information can be shared with an individual or group of people. Cognitive state information from an individual can be shared with another individual or group of people. In some embodiments, providing the aggregated cognitive state information to a requester is accomplished, while displaying the aggregated cognitive state information with the rendering is accomplished in other embodiments. This sharing of information can help people see what other people liked and disliked. Similarly, content can be recommended 662. For example, a video trailer which evoked a strong arousal and a positive valence can be recommended to others who share similar cognitive states for other video trailers. Additionally, an avatar can be animated 664 based on the cognitive states. The animation can be of just a face, a head, an upper half of a person, or a whole person. The animation can be based on an individual's cognitive state information. Alternatively, the animation can be based on the aggregated cognitive state information. In embodiments, cognitive state information for an individual is compared with the aggregated cognitive states. Differences between the individual and the aggregated cognitive states can be highlighted.

Figure 7:
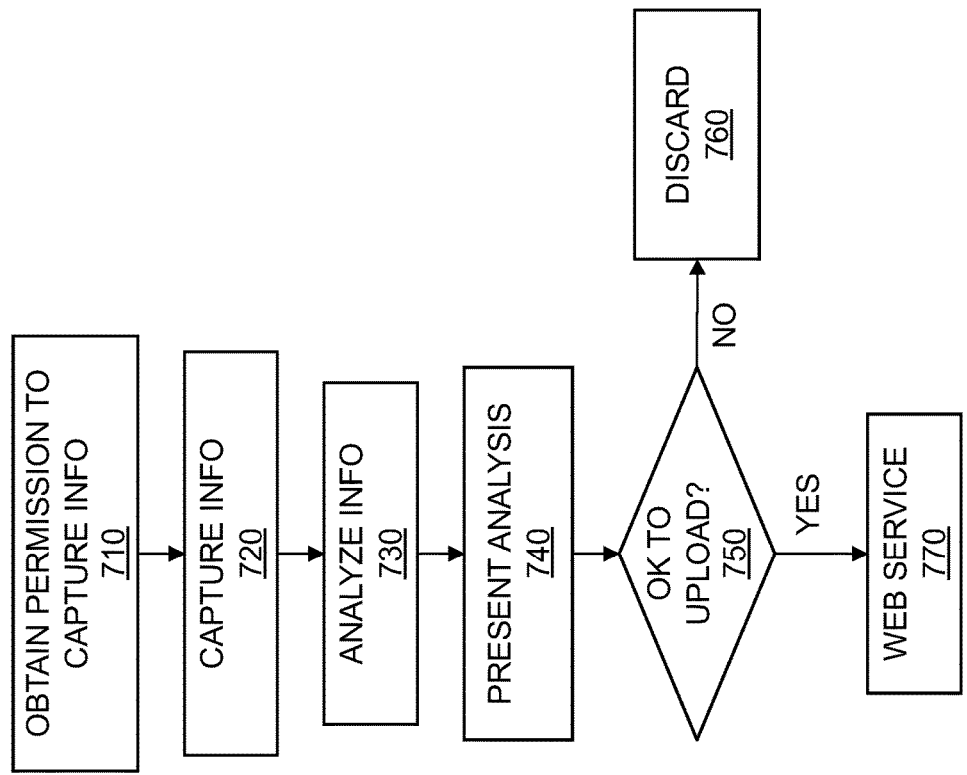
FIG. 7 is a flowchart for opting into analysis.

FIG. 7 is a flowchart for opting into analysis. The flow 700 can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. The flow 700 can begin with obtaining permission to capture information 710 from an individual. The information being captured can include facial data, physiological data, accelerometer data, or some other data obtained in the effort to infer cognitive states. In some embodiments, the permission requested is for the analysis of the information captured, such as the cognitive states inferred or other related results. In some embodiments, the permission is requested at another point or points in the flow 700. Likewise, permission can be requested at each step in the collection or analysis process.

The flow 700 continues with the capture of information 720. The information captured can include facial data, physiological data, accelerometer data, or some other data. The information is analyzed 730 to infer cognitive states. The analysis can involve client computer analysis of facial data, head gestures, physiological data, accelerometer data, and other collected data. The results of the analysis can be presented 740 to the individual. For example, the cognitive states and collected information can be presented. Based on the permission requested, the client computer can determine that it is acceptable to upload 750 the captured information and/or the analysis results. A further request for permission can be requested at this time, based on the presented analysis 740, such as to allow the opting-in by an individual from the plurality of people, or to allow uploading of cognitive state data. If permission is not obtained for uploading of the analysis or information, the analysis or information can be discarded 760. If the permission to upload is obtained, the information and/or analysis can be provided to a web service 770. The web service can provide additional analysis, aggregate the cognitive state information, or provide for sharing of the analysis or cognitive state information.

Figure 8:
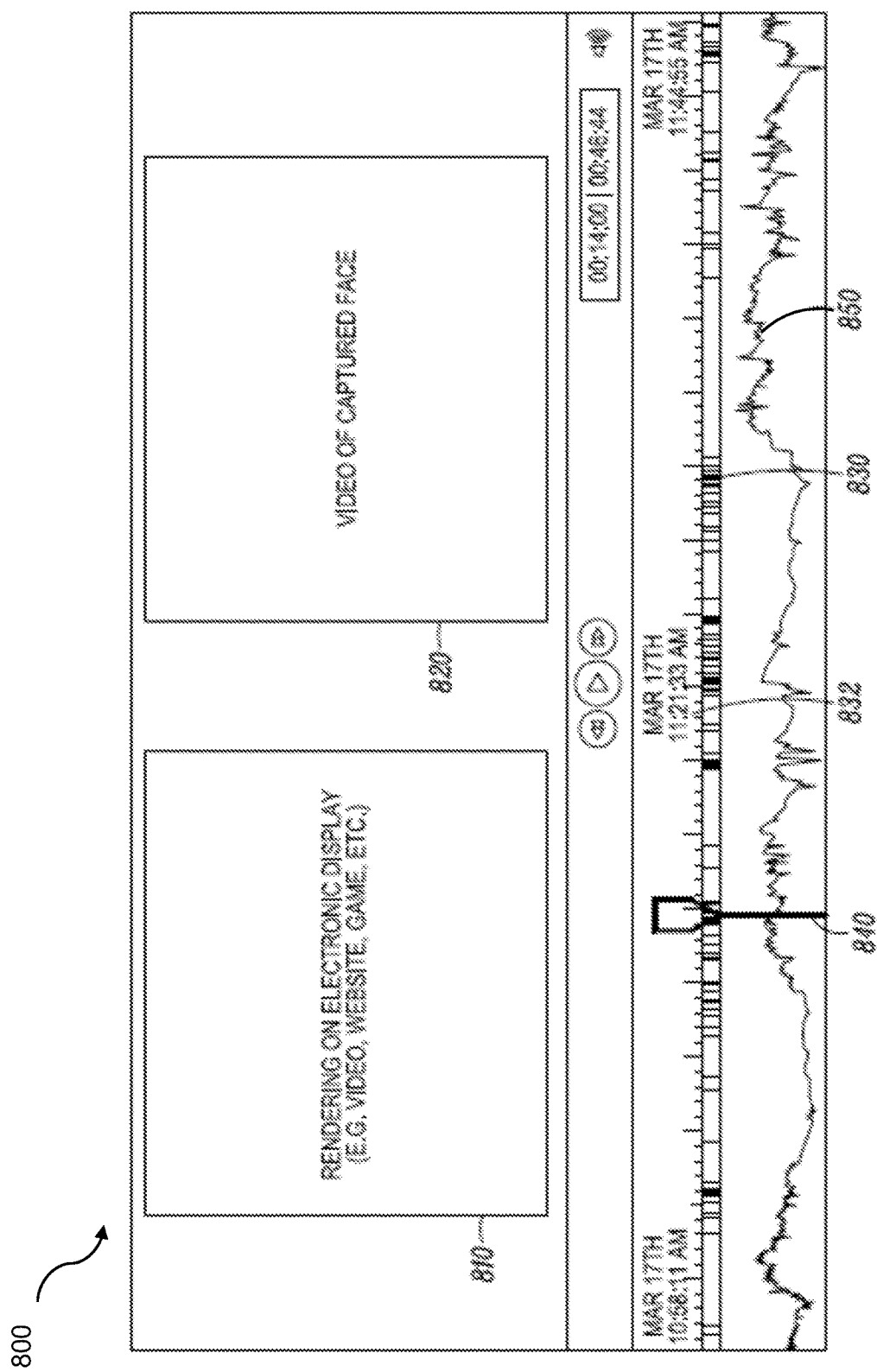
FIG. 8 is a representative diagram of a rendering and response.

FIG. 8 is a representative diagram of a rendering and response. A display window 800 can contain the rendering 810 along with video of the person viewing the rendering 820 and can also include one or more displays of additional information. In some embodiments, each of these portions is an individual floating window that can be repositioned as the user desires. The rendering on an electronic display 810 can be any type of rendering, including any rendering described herein, such as, without limitation, a landing page, a checkout page, a webpage, a website, a web-enabled application, a video on a web-enabled application, a game on a web-enabled application, or a virtual world. This rendering display 810 shows the user of the display window 800 the same rendering as the individual on whom cognitive state information was captured. In one example, the rendering can be a video and the video can play out in synch with the video of the captured face 820 for the individual. In some embodiments, the rendering 810 indicates where eyes are tracking. For instance, if the eyes of the individual viewing the rendering have been tracked to a particular button on a webpage, then the button can be highlighted. Alternatively, a box or oval can be shown on the rendering 810 which indicates the portion of the screen on which the person's eyes were focused. In this manner, the eye tracking will indicate the focus of the person, while the remainder of the window 800 can display cognitive state information about the person's reaction to the area of that focus.

Various information and analysis results can also be shown. In some embodiments, the additional information is shown in the display window 800 below the rendering 810 and the video 820. Any type of information can be shown, including cognitive state information from an individual, aggregated cognitive state information from a group of people, or other information about the rendering 810, the video 820, the individual or group of people from whom cognitive state information was captured, or any other type of information. Thus, a visual representation of one or more of the aggregated cognitive state information and cognitive state information on an individual from the plurality of people is created, in some embodiments. The cognitive state information can include any type of cognitive state information described herein, including electrodermal activity, accelerometer readings, frown markers, smile markers, as well as numerous other possible physiological and cognitive state indicators. By way of example, in the display window 800, a smile marker track 830 is provided. Where a narrow line on the smile marker track 830 exists, a hint of smile was detected. Where a solid dark line is shown, a broad smile, lasting for a while, was detected. This smile marker track can have a timeline 832, as shown, and the timeline 832 can also have a slider bar 840, as shown. The slider bar 840 can be moved to various points on the timeline 832 and the rendering 810 and the video 820 can each show what occurred at that point in time. By further example, an electrodermal activity track 850 is shown as well. While the display window 800 can show an individual, this window or set of windows can create a visual representation of the aggregated cognitive state information as well. For instance, once electrodermal activity information has been aggregated for a group of people, the aggregated electrodermal activity can be displayed for the rendering 810. As stated earlier, numerous displays of information and analysis are possible in this window or set of windows. These displays can be for the individual or for an aggregated group of people.

Figure 9:
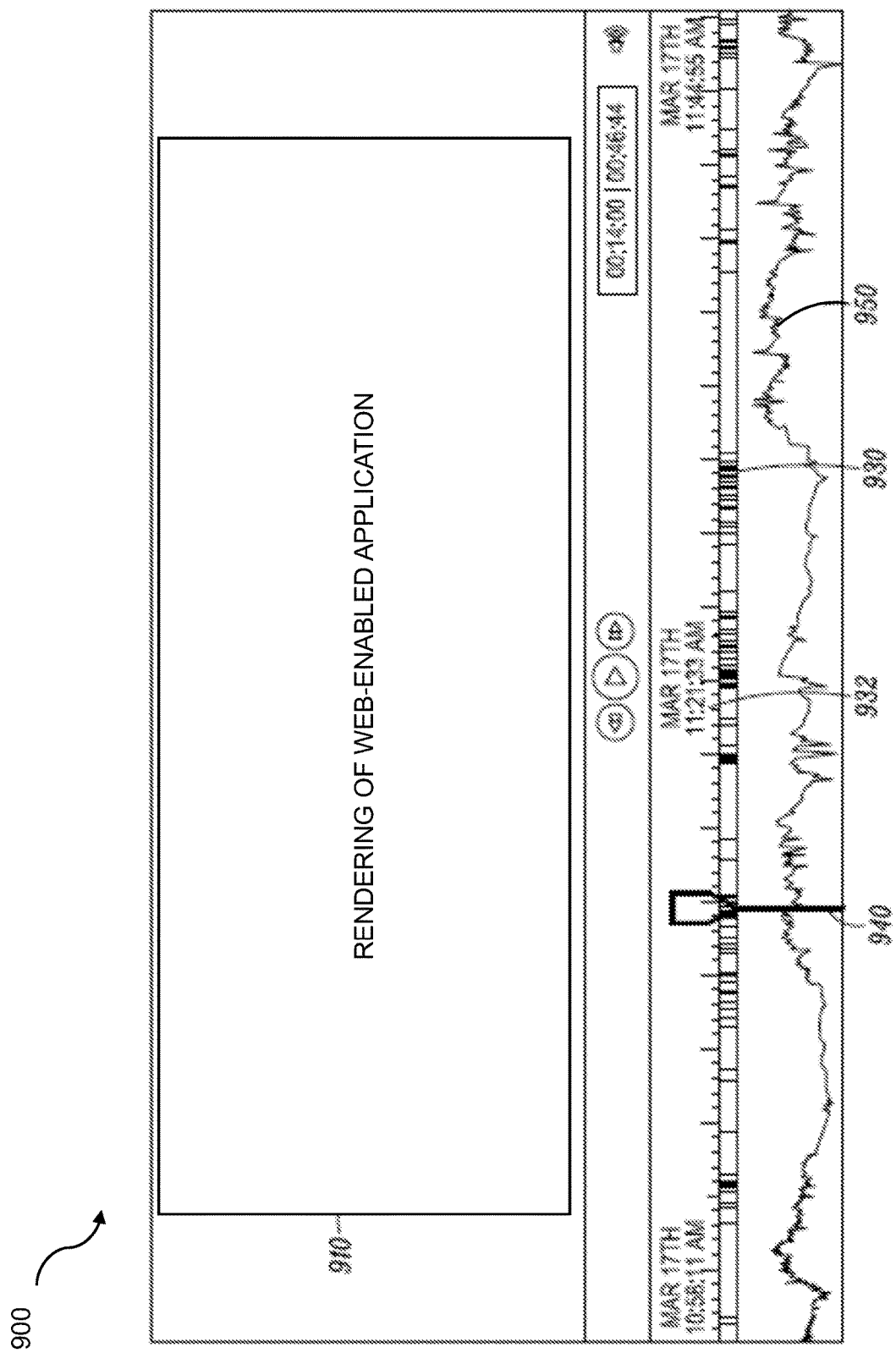
FIG. 9 is a representative diagram of a rendering and an aggregated response.

FIG. 9 is a representative diagram of a rendering and an aggregated response. A display window 900 can contain the rendering 910 of a web-enabled application. This rendering can be what was shown on an electronic display to multiple people. The rendering 910 can be any type of rendering, including any rendering described herein, such as, without limitation, a landing page, a checkout page, a webpage, a website, a mobile-device application, a cell-phone application, a web-enabled application, a video on a web-enabled application, a game on a web-enabled application, or a virtual world. This rendering 910 can show the user of the display window 900 the same rendering as the multiple people on whom cognitive state information was captured. In some embodiments, the rendering 910 indicates where a majority of eyes from the multiple people were tracking. For instance, a button can be highlighted or a box or oval which indicates the portion of the screen on which the majority of people's eyes were focused can be shown on the rendering 910.

Various information and aggregated analysis results can be shown including, for example, electrodermal activity, accelerometer readings, frown markers, smile markers, as well as numerous other possible physiological and cognitive state indicators. By way of example, in the display window 900, a smile marker track 930 is provided. Where a narrow line on the smile marker track 930 exists, a hint of smile was detected as a majority response of the multiple people. Where a solid dark line is shown, a broad smile that lasts for a long time was detected as a majority response of multiple people. This smile marker track can have a timeline 932, as shown, and the timeline 932 can also have a slider bar 940, as shown. The slider bar 940 can be moved to various points on the timeline 932 and the rendering 910 can show what occurred at that point in time, synchronizing the aggregated cognitive state information with the rendering. By further example, an aggregated electrodermal activity track 950 can also be included. As stated earlier, numerous displays of information and analysis are possible in this window or set of windows. In some embodiments, the portions are individual floating windows that can be repositioned as the user desires.

Figure 10:
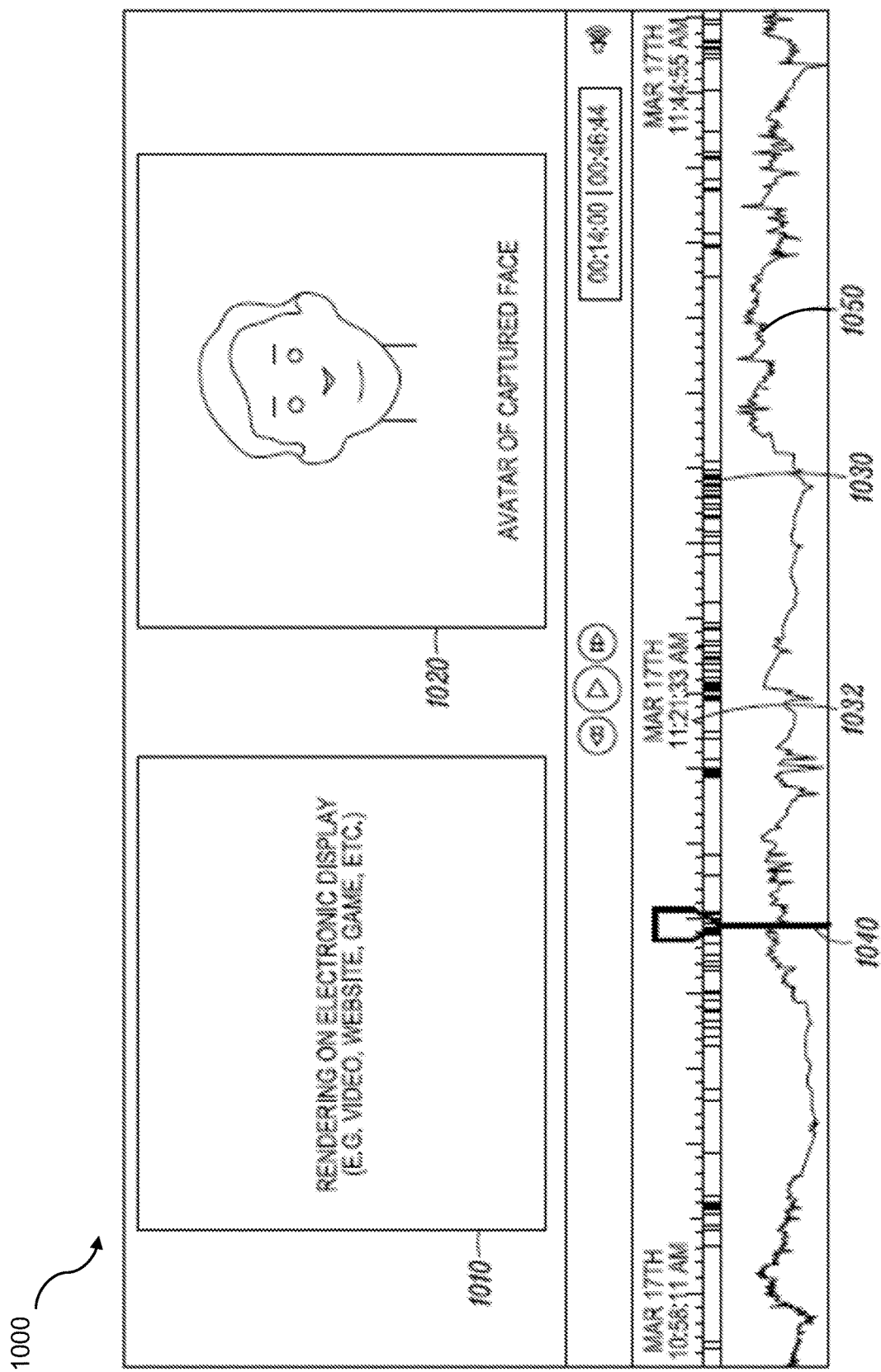
FIG. 10 is a representative diagram of a rendering and response with avatar.

FIG. 10 is a representative diagram of a rendering and response with avatar. A window 1000 can be shown which includes, for example, a display of a rendering 1010, an avatar of the captured face 1020, a smile track 1030, a timeline 1032, a slide bar 1040, and an electrodermal activity track 1050. Numerous other displays of information are possible as well. Each of the elements mentioned can be shown in the window 1000 or can be shown in another floating window. The avatar 1020 represents the person who viewed the rendering without showing video of the person. By using an avatar, a person's identity can be removed but indications of smiling, frowning, laughing, and other facial expressions can still be shown by means of the avatar. The avatar can show just a face, an entire head, an upper body, or a whole person. The avatar can, in some embodiments, reflect the characteristics of the individual that it represents, including gender, race, hair color, eye color, and various other aspects of the individual. In other embodiments, the concepts include animating an avatar to represent the aggregated cognitive state information. An avatar can then describe a group's response to the rendering 1010. For example, if the majority of people were engaged and happy, then the avatar might be shown with a smile and with a head that is tilted forward. As described above, some embodiments include animating an avatar to represent one or more of the aggregated cognitive state information and cognitive state information on an individual from the plurality of people.

Figure 11:
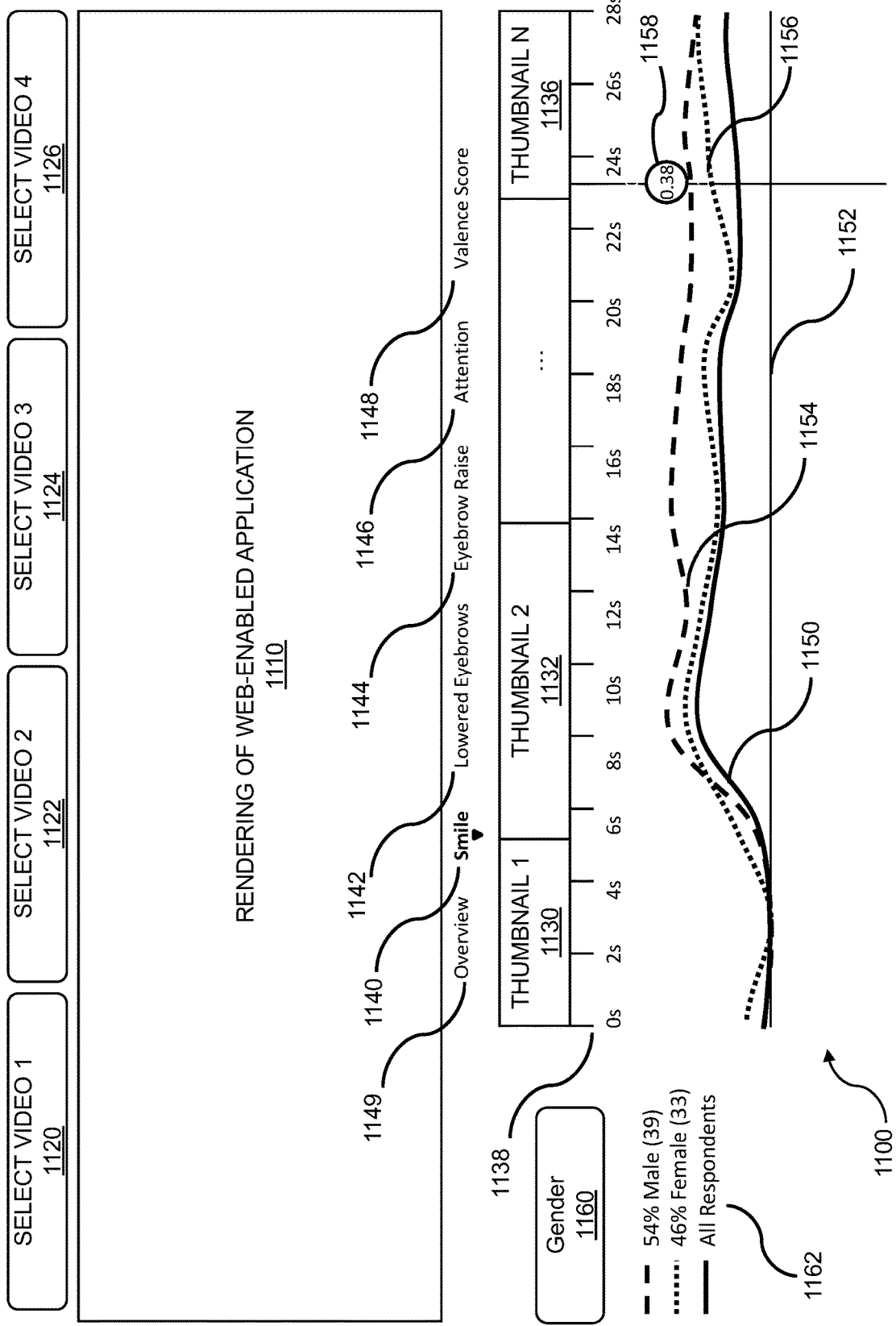
FIG. 11 is a graphical representation of cognitive state analysis.

FIG. 11 is a graphical representation of cognitive state analysis. A window 1100 can be shown which includes, for example, a rendering of the web-enabled application 1110 having associated cognitive state information. In the example shown, the rendering 1110 is a video, but can be any other type of rendering. A user can select between a plurality of renderings using various buttons and/or tabs, such as a Select Video 1 button 1120, a Select Video 2 button 1122, a Select Video 3 button 1124, and a Select Video 4 button 1126. Various embodiments have any number of selections available for the user and some are other types of renderings instead of video. A set of thumbnail images for the selected rendering, that in the example shown include a thumbnail 1 1130, a thumbnail 2 1132, through a thumbnail N 1136 can be shown below the rendering along with a timeline 1138. Some embodiments do not include thumbnails, or have a single thumbnail associated with the rendering, and various embodiments have thumbnails of equal length, while others have thumbnails of differing lengths. In some embodiments, the start and/or end of the thumbnails is determined by the editing cuts of the video of the rendering, while other embodiments determine a start and/or end of the thumbnails based on changes in the captured cognitive states associated with the rendering.

Some embodiments include the ability for a user to select a particular type of cognitive state information for display using various buttons or other selection methods. In the example shown, the smile cognitive state information is shown as the user might have previously selected the Smile button 1140. Other types of cognitive state information that are available for user selection in various embodiments include the Lowered Eyebrows button 1142, the Eyebrow Raise button 1144, the Attention button 1146, the Valence Score button 1148, or other types of cognitive state information, depending on the embodiment. An Overview button 1149 can be available to allow a user to show graphs of the multiple types of cognitive state information simultaneously.

Because the Smile option 1140 has been selected in the example shown, a smile graph 1150 can be shown against a baseline 1152 showing the aggregated smile cognitive state information of the plurality of individuals from whom cognitive state data was collected for the rendering 1110. A male smile graph 1154 and a female smile graph 1156 can be shown so that the visual representation displays the aggregated cognitive state information on a demographic basis. The various demographic-based graphs can be indicated using various line types, as shown, or can be indicated using color or another method of differentiation. A slider 1158 can allow a user to select a particular time of the timeline and can show the value of the chosen cognitive state for that particular time. The slider can show the same line type or color as the demographic group whose value is shown.

In some embodiments, various types of demographic based cognitive state information are selected using the demographic button 1160. Such demographics can include gender, age, race, income level, or any other type of demographic, including dividing the respondents into those respondents that had a higher reaction from those with lower reactions. A graph legend 1162 can be displayed indicating the various demographic groups, the line type or color for each group, the percentage of total respondents or absolute number of respondents for each group, and/or other information about the demographic groups. The cognitive state information can be aggregated according to the demographic type selected. Thus, for some embodiments, aggregation of the aggregated cognitive state information is performed on a demographic basis so that cognitive state information is grouped based on the demographic basis.

Figure 12:
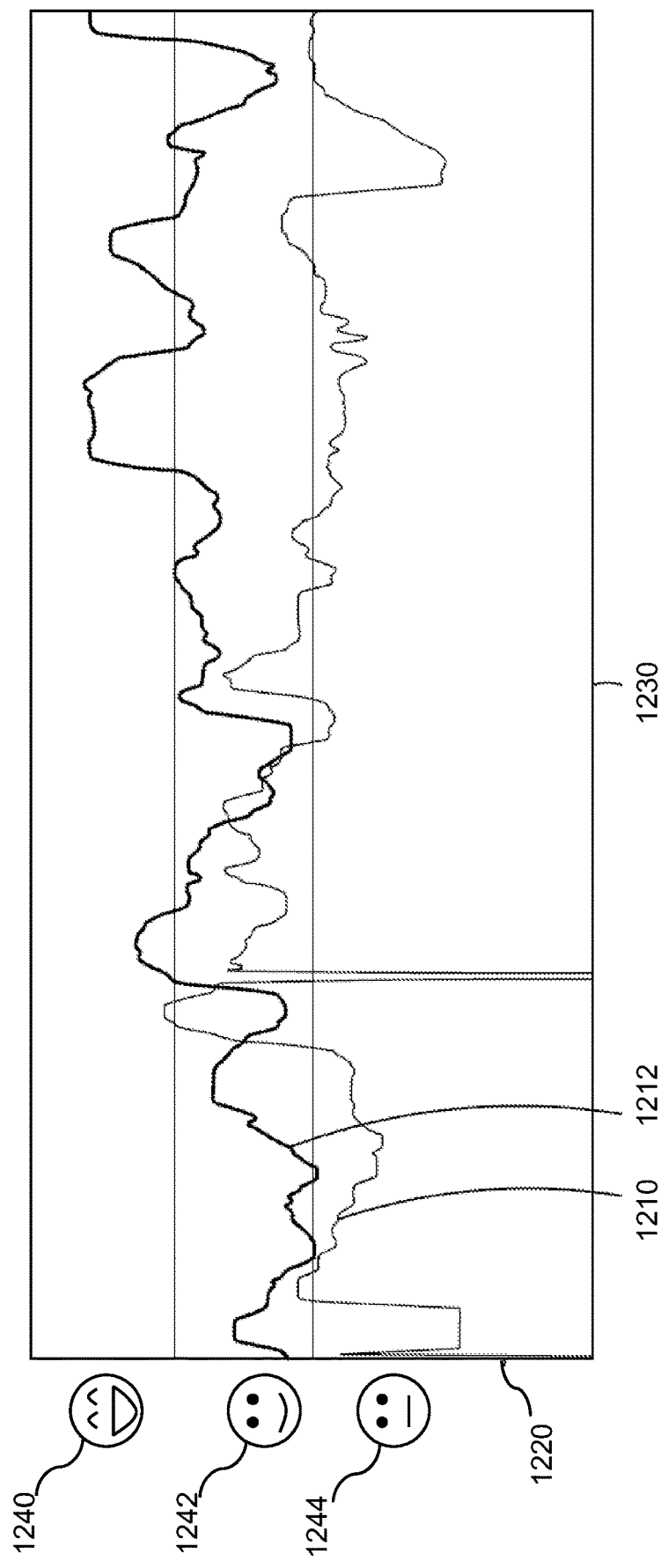
FIG. 12 is a graphical representation of cognitive state analysis along with an aggregated result from a group of people.

FIG. 12 is a graphical representation of cognitive state analysis along with an aggregated result from a group of people. This rendering can be displayed on a webpage, a web-enabled application, or another type of electronic display representation. A graph 1210 can be shown for an individual on whom affect data is collected. Another graph 1212 can be shown for affect collected on another individual or aggregated affect from multiple people. The cognitive state analysis can be based on facial image or physiological data collection. In some embodiments, the graph 1210 indicates the amount or probability of a smile being observed for the individual. A higher value or point on the graph can indicate a stronger or larger smile. In certain spots, the graph can drop out or degrade when image collection was lost or was not able to identify the face of the person. The probability or intensity of an affect can be given along the y-axis 1220. A timeline can be given along the x-axis 1230. The aggregated information can be based on taking the average, median, or another statistical or calculated value based on the information collected from a group of people. In some embodiments, aggregation of the aggregated cognitive state information is accomplished using computational aggregation.

In some embodiments, graphical smiley face icons 1240, 1242, and 1244 are shown, providing an indication of the amount of a smile or another facial expression. A first very broad smiley face icon 1240 can indicate a very large smile being observed. A second normal smiley face icon 1242 can indicate a smile being observed. A third face icon 1244 can indicate no smile. Each of the icons can correspond to a region on the y-axis 1220 that indicate the probability or intensity of a smile.

Figure 13:
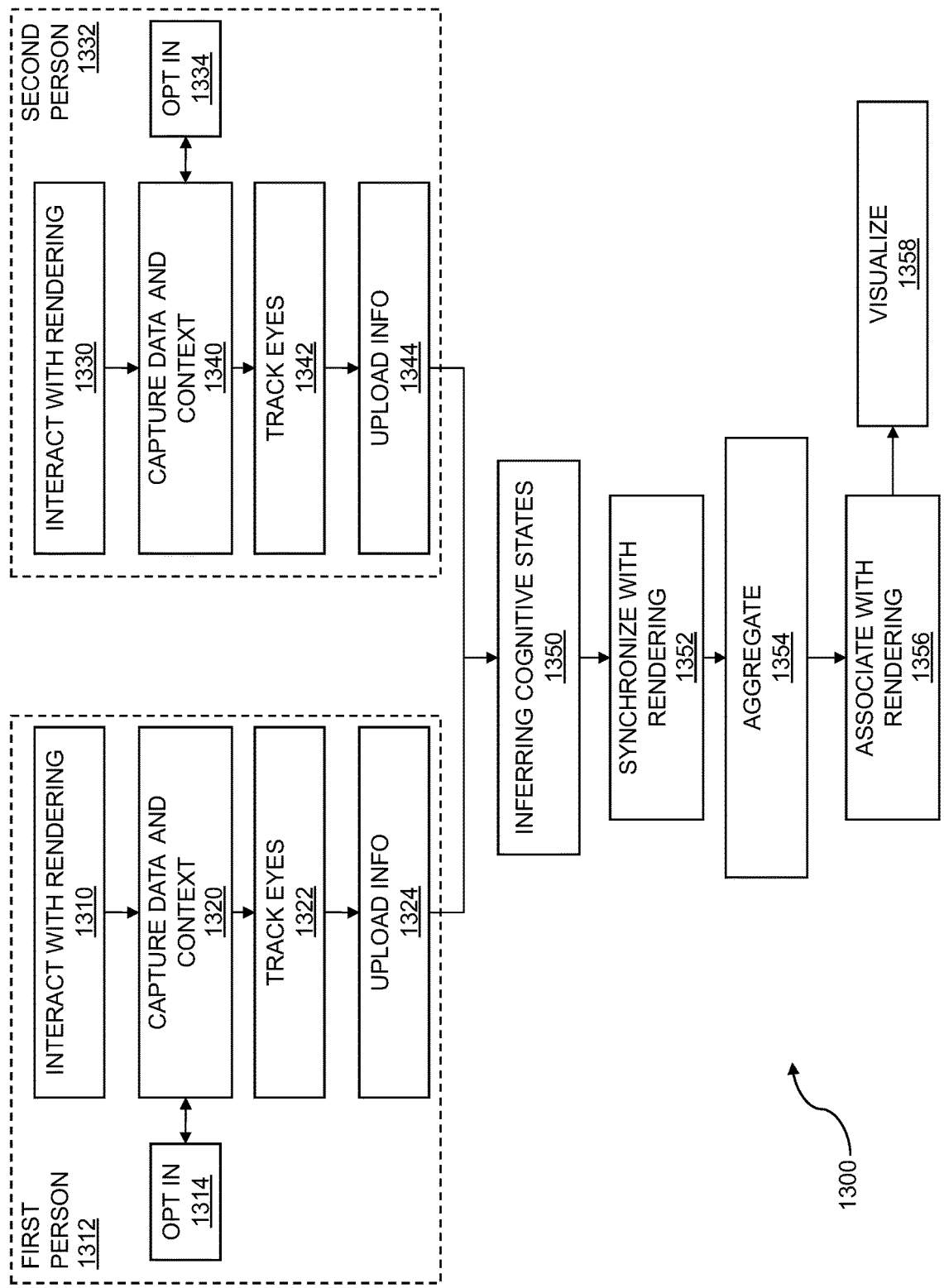
FIG. 13 is a flowchart for analyzing affect from rendering interaction.

FIG. 13 is a flowchart for analyzing affect from rendering interaction. The flow 1300 can enable remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. The flow 1300 for analyzing renderings on electronic displays begins with interacting with a rendering 1310 on an electronic display by a first person 1312. The rendering can be any type of rendering, including those renderings described herein. In some embodiments, there is a query for the first person 1312 to opt in 1314 to the process of capturing data. If allowable by the first person, the flow 1300 can continue by capturing context and capturing data 1320 on the first person into a computer system as the first person interacts with the rendering on the electronic display. In some embodiments, capturing data involves capture of one of a group comprising physiological data and facial data. The captured data can include electrodermal, accelerometer, and/or other data. The captured context can be a timeline, a sequence of webpages, or some other indicator of what is occurring in the web-enabled application.

The eyes can be tracked 1322 to determine where the first person 1312 is focused on the display. The flow 1300 includes uploading information 1324 on the data which was captured on the first person to a server. Permission can again be solicited and granted before the upload of information occurs.

The flow 1300 continues with interacting with the rendering 1330 by a second person 1332. In some embodiments, there is a query for the second person 1332 to opt in 1334 to the process of capturing data. If allowable by the second person, the flow 1300 can continue by capturing context and capturing data 1340 on the second person as the second person interacts with the rendering. The eyes can be tracked 1342 to determine where the second person 1332 is focused on the display. The flow 1300 can include uploading information 1344 to the server on the data which was captured on the second person. Permission can again be solicited before the upload of information.

The flow 1300 continues with the inferring of cognitive states 1350 for the first person who interacted with the rendering, based on the data which was captured for the first person, and inferring of cognitive states 1350 for the second person who interacted with the rendering, based on the data which was captured for the second person. This inferring 1350 can be done on the client computers of the first and second person, respectively. Alternatively, the inferring of cognitive states 1350 can be performed on the server computer after the upload of information or on some other computer with access to the uploaded information. The inferring of cognitive states can be based on one of a group comprising physiological data and facial data, in some embodiments, and can include inferring of cognitive states based on the cognitive state data collected from the plurality of people. The inferring of cognitive states is based on both physiological data and facial data, in some embodiments. The cognitive states can be synchronized with the rendering 1352. In one embodiment, this synchronization correlates the cognitive states with a timeline that is part of a video. In embodiments, the synchronization correlates the cognitive states with a specific web page or a certain sequence of web pages. The synchronization 1352 can be performed on the first and second person's client computers respectively, can be performed on a server computer after uploading, or can be performed by some other computer.

The flow 1300 continues with aggregating 1354 information on the cognitive states of the first person with the cognitive states of the second person, resulting in aggregated cognitive state information. The aggregating 1354 can include computational aggregation. The aggregation can be performed using one or more processors. The aggregation can include combining electrodermal activity or other readings from multiple people. The flow 1300 continues with associating to the rendering 1356 the aggregated cognitive state information with which the first person and the second person interacted. The associating of the aggregated cognitive state information allows recall and further analysis of the rendering and peoples' cognitive state reactions to the rendering. The flow 1300 continues with visualization 1358 of the aggregated and/or associated cognitive state information. This visualization can include a graphical or textual presentation. The visualization can also include a presentation in the form of an avatar. The flow 1300 can continue with any number of people's data being captured, cognitive states being inferred, and all other steps in the flow.

Figure 14:
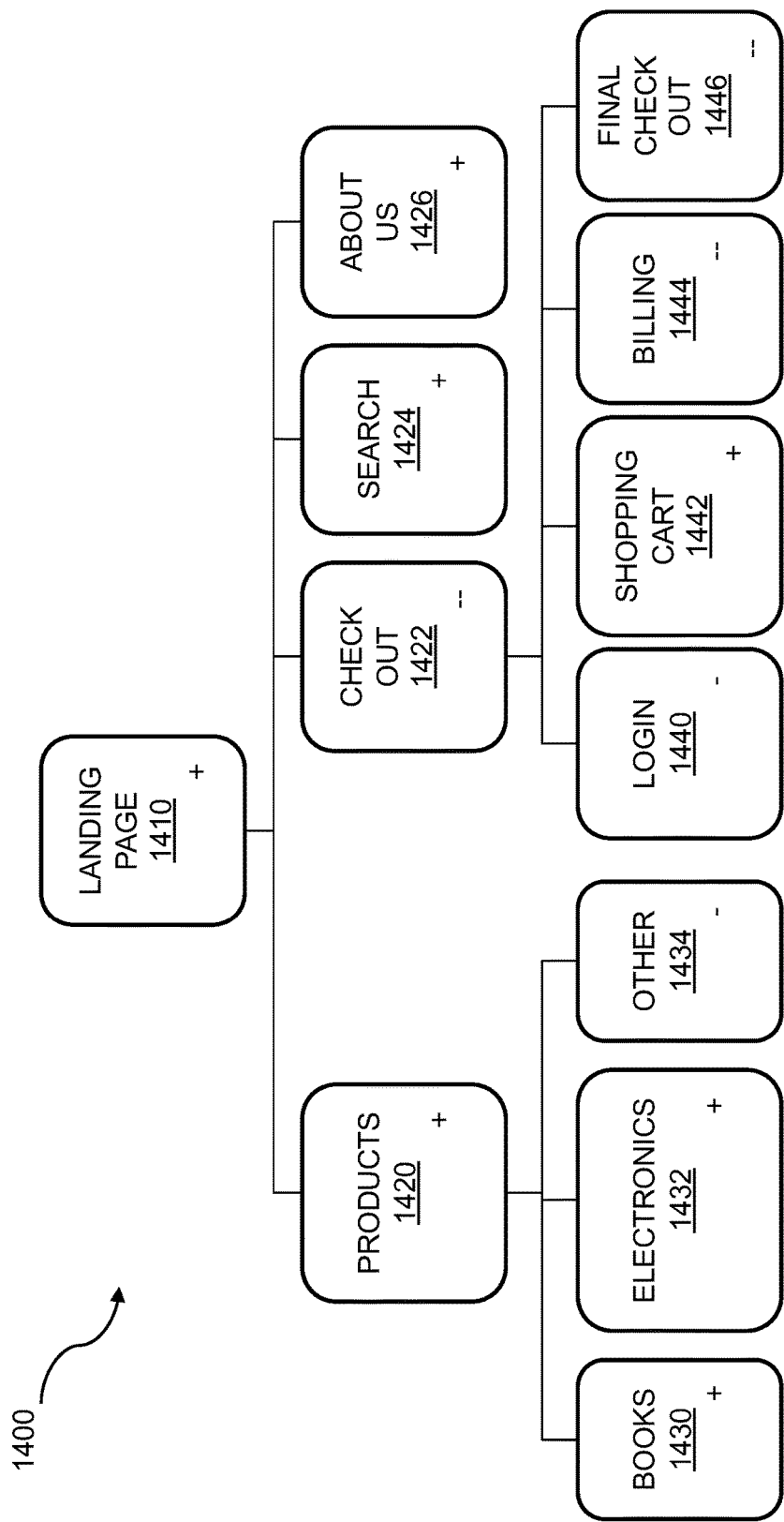
FIG. 14 is an example embodiment of a visual representation of cognitive states.

FIG. 14 is an example of a visual representation of cognitive states, showing a series of web pages 1400 with which there has been interaction. These web pages include a landing page 1410, a products page 1420, a checkout page 1422, a search page 1424, and an "about us" page 1426. Some of these pages can in turn have sub-pages, such as the products page 1420, which has sub-pages of a books page 1430, an electronics page 1432, and other product pages represented by the other page 1434. In some embodiments, one or more of these pages have further sub-pages. Furthermore, the checkout page 1422 has sub-pages of a login page 1440, a shopping cart page 1442, a billing page 1444, and a final checkout page 1446. As an individual interacts with these pages, cognitive states can be inferred. Further, as multiple people interact with these pages, aggregated information on inferred cognitive states can be accumulated. Detailed results can be accumulated on each of these pages. These detailed results can be presented. Alternatively, a simplified analysis can be presented that gives positive, slightly negative, and negative indications. In some embodiments, very positive or neutral responses are also being shown. In the series of web pages 1400, a positive impression is shown as a "+" in the lower right corner of the web page box, such as the landing page 1410. A "+" can denote a positive cognitive state for an individual or aggregated group of people. A slightly negative response can be denoted by a "−" in the bottom right of the web page box, such as the login page 1440. A "−" can indicate confusion. A very negative reaction can be indicated by a "−−" in the lower right corner of the webpage box, such as the billing page 1444. A "−−" can denote anger, frustration, or disappointment. In some embodiments, colors are used to represent the positive, slightly negative, and very negative reactions. Such colors can be green, yellow, and red, respectively. Any of the methods described, or other methods of displaying the aggregated cognitive state information, can be used for creating a visual representation of the aggregated cognitive state information.

Figure 15:
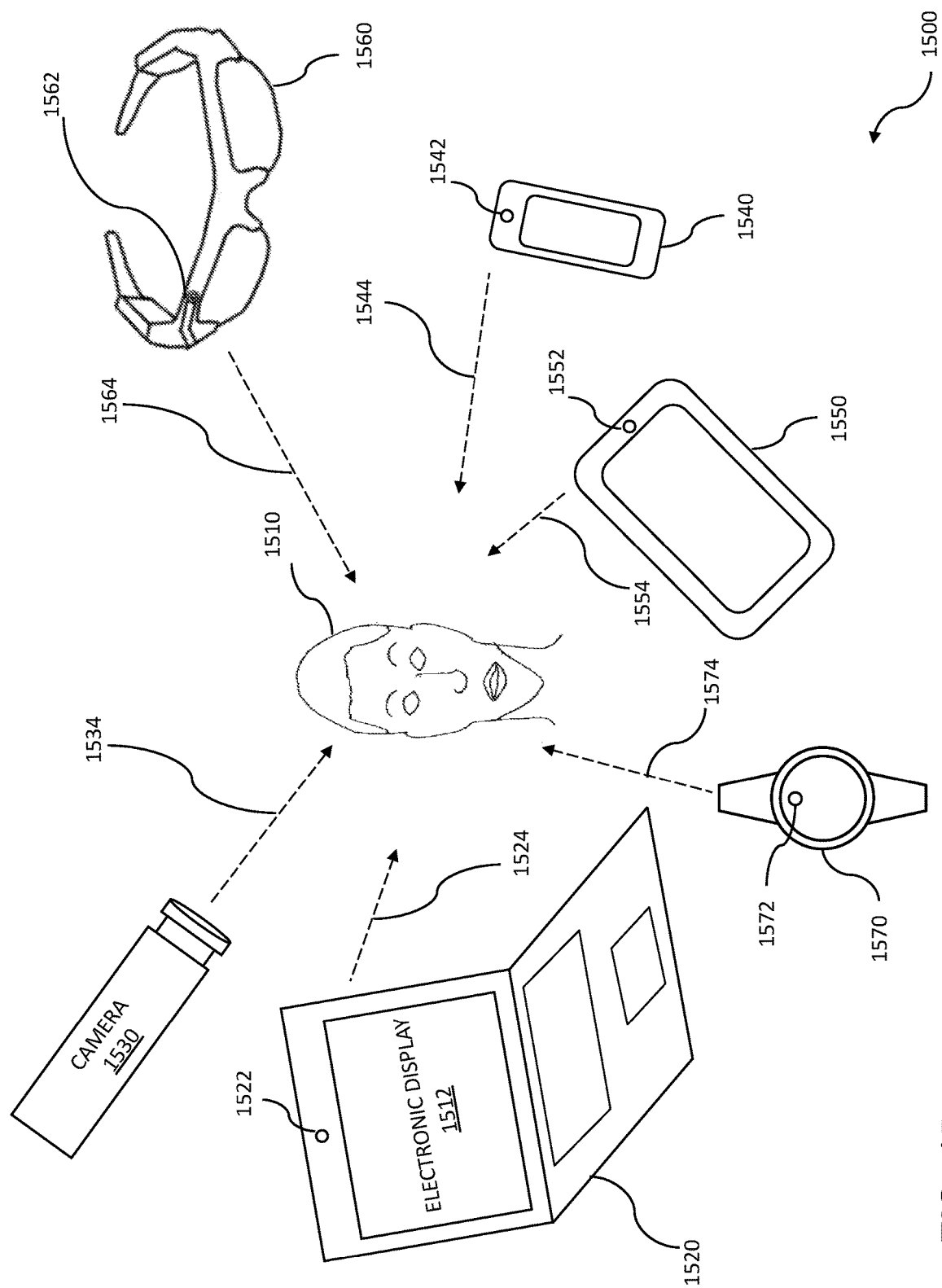
FIG. 15 is a diagram showing image collection including multiple mobile devices.

FIG. 15 is a diagram showing image collection including multiple mobile devices. Image collection including multiple mobile devices can enable remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people.

In the diagram 1500, the multiple mobile devices can be used singly or together to collect video data on a user 1510. While one person is shown, the video data can be collected on multiple people. A user 1510 can be observed as she or he is performing a task, experiencing an event, viewing a media presentation, and so on. The user 1510 can be shown one or more media presentations, political presentations, social media, or another form of displayed media. The one or more media presentations can be shown to a plurality of people. The media presentations can be displayed on an electronic display 1512 or another display. The data collected on the user 1510 or on a plurality of users can be in the form of one or more videos, video frames, still images, etc. The plurality of videos can be of people who are experiencing different situations. Some example situations can include the user or plurality of users being exposed to TV programs, movies, video clips, social media, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1510 can be analyzed and viewed for a variety of purposes including expression analysis, cognitive state analysis, and so on. The electronic display 1512 can be on a laptop computer 1520 as shown, a tablet computer 1550, a cell phone 1540, a television, a mobile monitor, or any other type of electronic device. In one embodiment, expression data is collected on a mobile device such as a cell phone 1540, a tablet computer 1550, a laptop computer 1520, or a watch 1570. Thus, the multiple sources can include at least one mobile device, such as a phone 1540 or a tablet 1550, or a wearable device such as a watch 1570 or glasses 1560. A mobile device can include a forward-facing camera and/or a rear-facing camera that can be used to collect expression data. Sources of expression data can include a webcam 1522, a phone camera 1542, a tablet camera 1552, a wearable camera 1562, and a mobile camera 1530. A wearable camera can comprise various camera devices, such as a watch camera 1572.

As the user 1510 is monitored, the user 1510 might move due to the nature of the task, boredom, discomfort, distractions, or for another reason. As the user moves, the camera with a view of the user's face can be changed. Thus, as an example, if the user 1510 is looking in a first direction, the line of sight 1524 from the webcam 1522 is able to observe the user's face, but if the user is looking in a second direction, the line of sight 1534 from the mobile camera 1530 is able to observe the user's face. Furthermore, in other embodiments, if the user is looking in a third direction, the line of sight 1544 from the phone camera 1542 is able to observe the user's face, and if the user is looking in a fourth direction, the line of sight 1554 from the tablet camera 1552 is able to observe the user's face. If the user is looking in a fifth direction, the line of sight 1564 from the wearable camera 1562, which can be a device such as the glasses 1560 shown and can be worn by another user or an observer, is able to observe the user's face. If the user is looking in a sixth direction, the line of sight 1574 from the wearable watch-type device 1570, with a camera 1572 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1510 can also use a wearable device including a camera for gathering contextual information and/or collecting expression data on other users. Because the user 1510 can move her or his head, the facial data can be collected intermittently when she or he is looking in a direction of a camera. In some cases, multiple people can be included in the view from one or more cameras, and some embodiments include filtering out faces of one or more other people to determine whether the user 1510 is looking toward a camera. All or some of the expression data can be continuously or sporadically available from the various devices and other devices.

The captured video data can include facial expressions and can be analyzed on a computing device such as the video capture device or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and can be sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 16:
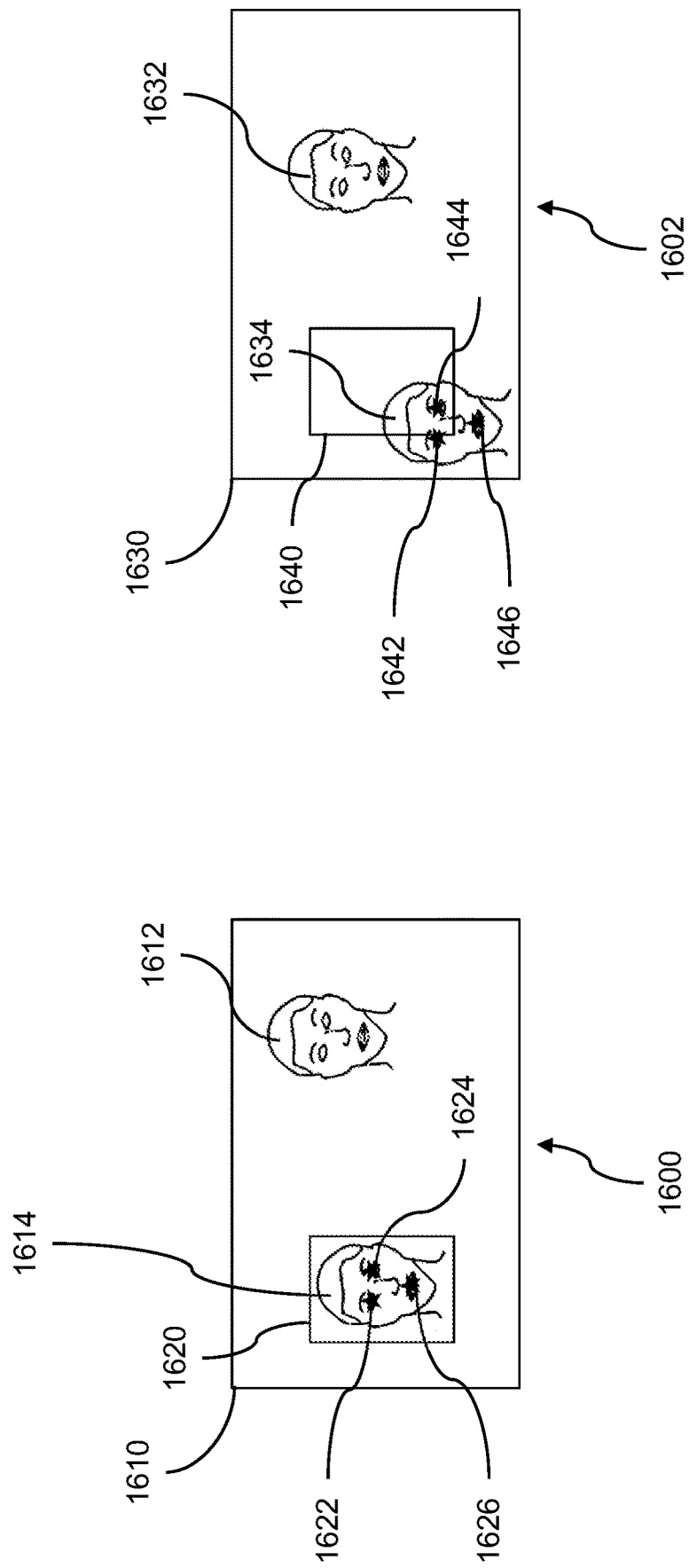
FIG. 16 illustrates feature extraction for multiple faces.

FIG. 16 illustrates feature extraction for multiple faces. The feature extraction for multiple faces can be performed for faces that can be detected in multiple images. The feature extraction for multiple faces can be performed for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. In embodiments, the features of multiple faces are extracted for evaluating cognitive states. Features of a face or a plurality of faces can be extracted from collected video data. Feature extraction for multiple faces can be based on sub-sectional components. The sub-sectional components can be used with performing the evaluation of content of the face. The sub-sectional components can be used to provide a context. The feature extraction can be performed by analysis using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When the new observation is received, then the classifier can be used to categorize the new observation. Classifiers can be used for many analysis applications, including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques for performing classification exist. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 16, the detection of the first face, the second face, and multiple faces can include identifying facial landmarks, generating a bounding box, and prediction of a bounding box and landmarks for a next frame, where the next frame can be one of a plurality of frames of a video containing faces. A first video frame 1600 includes a frame boundary 1610, a first face 1612, and a second face 1614. The video frame 1600 also includes a bounding box 1620. Facial landmarks can be generated for the first face 1612. Face detection can be performed to initialize a second set of locations for a second set of facial landmarks for a second face within the video. Facial landmarks in the video frame 1600 can include the facial landmarks 1622, 1624, and 1626. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 1620. Bounding boxes can also be estimated for one or more other faces within the boundary 1610. The bounding box can be refined, as can one or more facial landmarks. The refining of the second set of locations for the second set of facial landmarks can be based on localized information around the second set of facial landmarks. The bounding box 1620 and the facial landmarks 1622, 1624, and 1626 can be used to estimate future locations for the second set of locations for the second set of facial landmarks in a future video frame from the first video frame.

A second video frame 1602 is also shown. The second video frame 1602 includes a frame boundary 1630, a first face 1632, and a second face 1634. The second video frame 1602 also includes a bounding box 1640 and the facial landmarks, or points, 1642, 1644, and 1646. In other embodiments, multiple facial landmarks are generated and used for facial tracking of the two or more faces of a video frame, such as the shown second video frame 1602. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, multiple facial points can be determined within a frame. One or more of the other facial points that are determined can correspond to a third face. The location of the bounding box 1640 can be estimated, where the estimating can be based on the location of the generated bounding box 1620 shown in the first video frame 1600. The three facial points shown, facial points, or landmarks, 1642, 1644, and 1646, might lie within the bounding box 1640 or might not lie partially or completely within the bounding box 1640. For instance, the second face 1634 might have moved between the first video frame 1600 and the second video frame 1602. Based on the accuracy of the estimating of the bounding box 1640, a new estimation for a third, future frame from the video, and so on can be determined. The evaluation can be performed, all or in part, on semiconductor-based logic.

Figure 17:
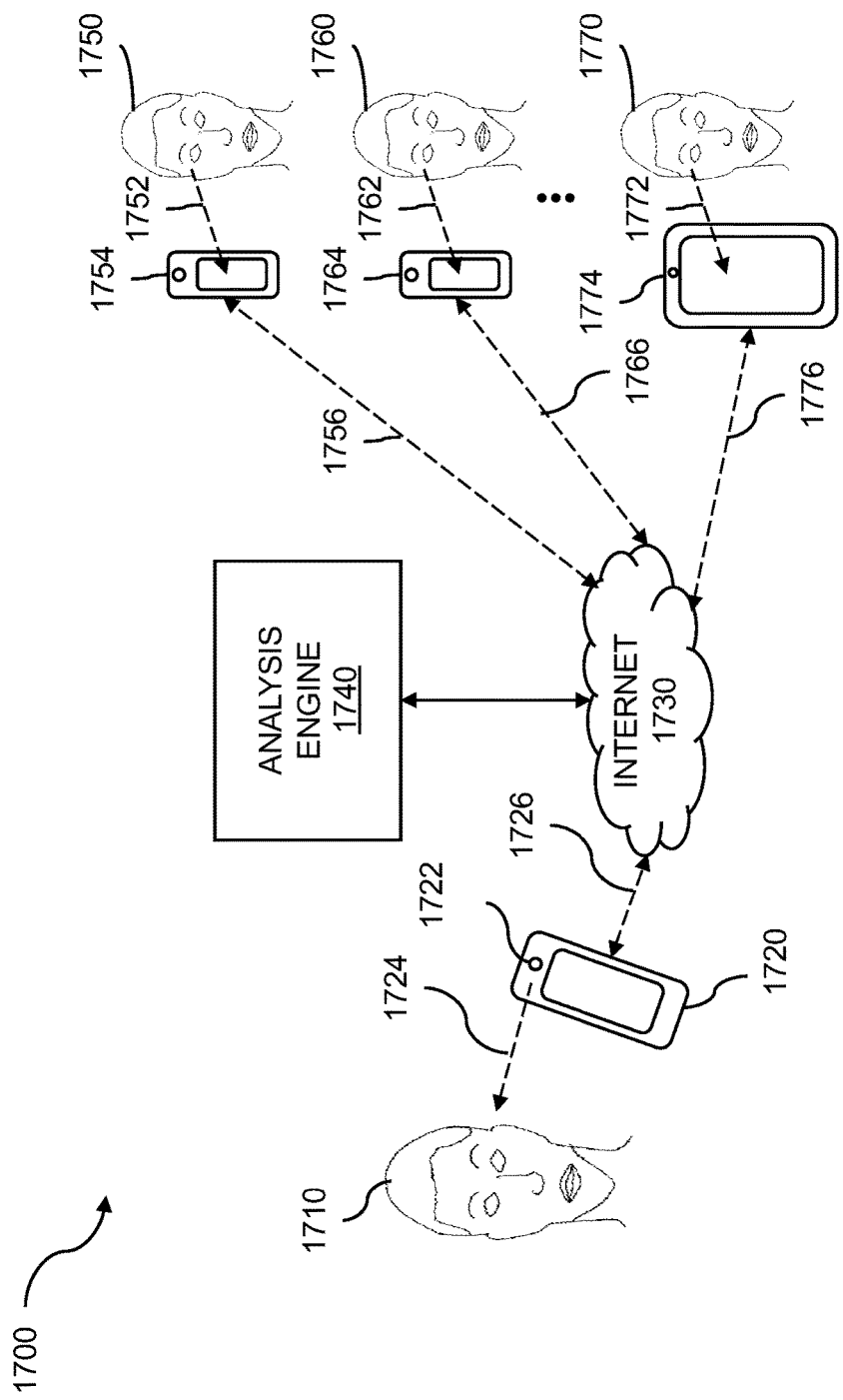
FIG. 17 shows livestreaming of social video.

FIG. 17 shows livestreaming of social video. The live streaming of social video can be performed for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. The streaming and analysis can be facilitated by a video capture device, a local server, a remote server, semiconductor-based logic, and so on. The streaming can be livestreaming and can include cognitive state analysis, cognitive state event signature analysis, etc. Livestreaming video is an example of one-to-many social media, where video can be sent over the Internet from one person to a plurality of people using a social media app and/or platform. Livestreaming is one of numerous popular techniques used by people who want to disseminate ideas, send information, provide entertainment, share experiences, and so on. Some of the livestreams such as webcasts, online classes, sporting events, news, computer gaming, or video conferences can be scheduled, while others can be impromptu streams that are broadcast as needed or when desired. Examples of impromptu livestream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, "reporters" can use networked, portable electronic devices to provide mobile journalism content to a plurality of social media followers. Such reporters can be quickly and inexpensively deployed as the need or desire arises.

Several livestreaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the livestream can comment on the stream using tweets that can be seen and responded to by the broadcaster. Another popular app is Periscope™ that can transmit a live recording from one user to that user's Periscope™ account and other followers. The Periscope™ app can be executed on a mobile device. The user's Periscope™ followers can receive an alert whenever that user begins a video transmission. Another livestream video platform is Twitch™ that can be used for video streaming of video gaming and broadcasts of various competitions and events.

The example 1700 shows a user 1710 broadcasting a video livestream to one or more people as shown by a first person 1750, a second person 1760, and a third person 1770. A portable, network-enabled, electronic device 1720 can be coupled to a forward-facing camera 1722. The portable electronic device 1720 can be a smartphone, a PDA, a tablet, a laptop computer, and so on. The camera 1722 coupled to the device 1720 can have a line-of-sight view 1724 to the user 1710 and can capture video of the user 1710. The captured video can be sent to an analysis or recommendation engine 1740 using a network link 1726 to the Internet 1730. The network link can be a wireless link, a wired link, and so on. The recommendation engine 1740 can recommend to the user 1710 an app and/or platform that can be supported by the server and can be used to provide a video livestream to one or more followers of the user 1710. In the example 1700, the user 1710 has three followers: a first person 1750, a second person 1760, and a third person 1770. Each follower has a line-of-sight view to a video screen on a portable, networked electronic device. In other embodiments, one or more followers follow the user 1710 using any other networked electronic device, including a computer. In the example 1700, the first person 1750 has a line-of-sight view 1752 to the video screen of a device 1754; the second person 1760 has a line-of-sight view 1762 to the video screen of a device 1764, and the third person 1770 has a line-of-sight view 1772 to the video screen of a device 1774. The portable electronic devices 1754, 1764, and 1774 can each be a smartphone, a PDA, a tablet, and so on. Each portable device can receive the video stream being broadcast by the user 1710 through the Internet 1730 using the app and/or platform that can be recommended by the recommendation engine 1740. The device 1754 can receive a video stream using the network link 1756, the device 1764 can receive a video stream using the network link 1766, the device 1774 can receive a video stream using the network link 1776, and so on. The network link can be a wireless link, a wired link, a hybrid link, and so on. Depending on the app and/or platform that can be recommended by the recommendation engine 1740, one or more followers, such as the followers 1750, 1760, 1770, and so on, can reply to, comment on, and otherwise provide feedback to the user 1710 using their devices 1754, 1764, and 1774, respectively.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt in to the video data collection.

The videos captured from the various viewers who chose to opt in can be substantially different in terms of video quality, frame rate, etc. As a result, the facial video data can be scaled, rotated, and otherwise adjusted to improve consistency. Human factors further influence the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data.

The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the observed person. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity, as well as specific emotions, moods, or cognitive states, are evaluated.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers, including classifiers such as support vector machines (SVM) and random forests, perform the classification. Random forests can include ensemble-learning methods that use multiple learning algorithms to obtain better predictive performance. Frame-by-frame detection can be performed to recognize the presence of an asymmetric expression in each frame of a video. Facial points, including the top of the mouth and the two outer eye corners, can be detected. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBPs) and Local Gabor Binary Patterns (LGBPs). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 18:
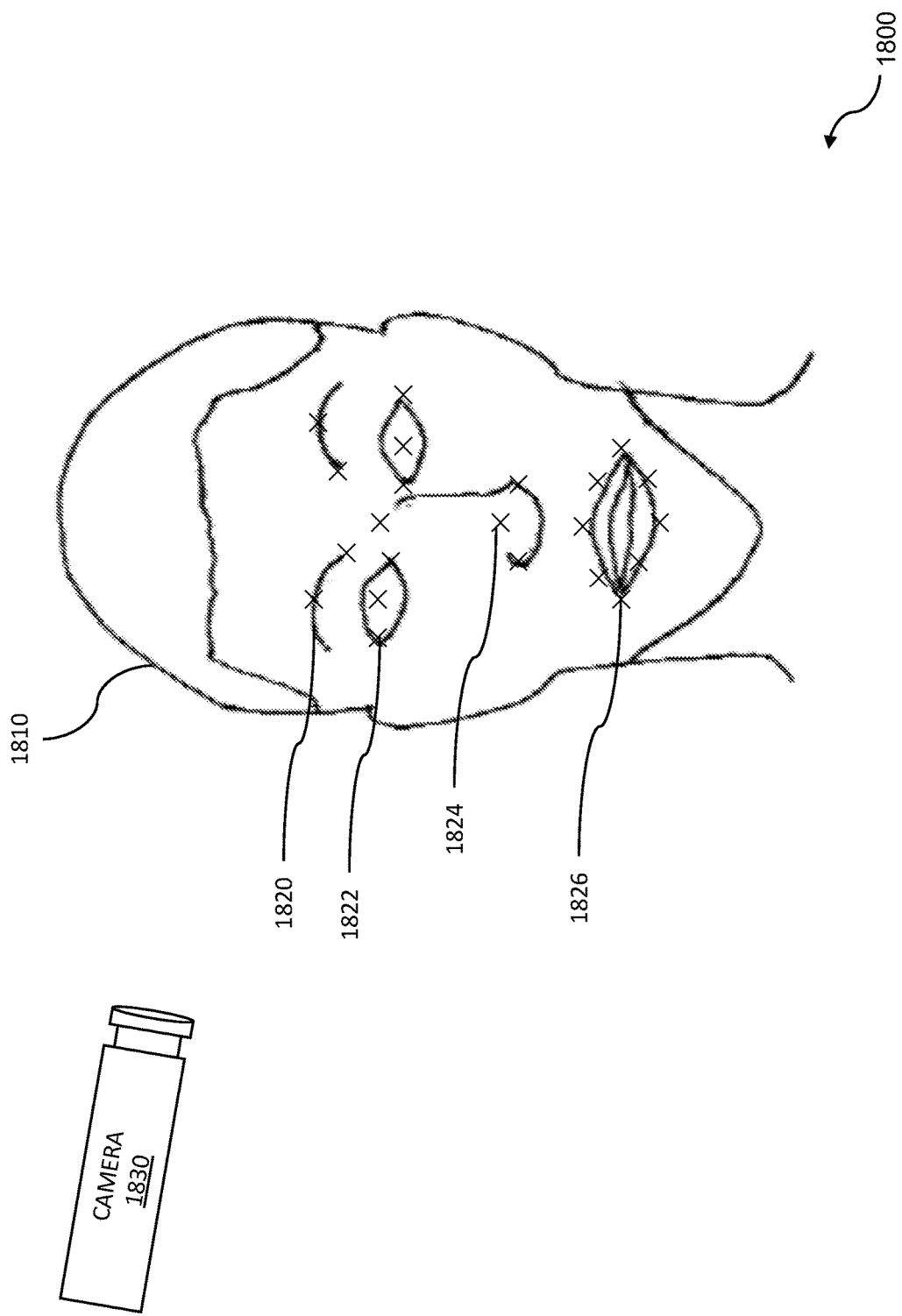
FIG. 18 shows example facial data collection including landmarks.

FIG. 18 shows example facial data collection including landmarks. The collecting of facial data including landmarks can be performed for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. In the example 1800, facial data including facial landmarks can be collected using a variety of electronic hardware and software techniques. The collecting of facial data including landmarks can be based on sub-sectional components of a population. The sub-sectional components can be used with performing the evaluation of content of the face, identifying facial landmarks, etc. The sub-sectional components can be used to provide a context. A face 1810 can be observed using a camera 1830 in order to collect facial data that includes facial landmarks. The facial data can be collected from a plurality of people using one or more of a variety of cameras. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend on the position of the camera 1830 relative to the face 1810, the number of cameras used, the illumination of the face, etc. In some cases, if the face 1810 is poorly lit or over-exposed (e.g. in an area of bright light), the processing of the facial data to identify facial landmarks might be rendered more difficult. In another example, the camera 1830 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 1820, an outer eye edge 1822, a nose 1824, a corner of a mouth 1826, and so on. Multiple facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Multiple action units can be identified. The action units can be used alone and/or in combination to infer one or more cognitive states and emotions. A similar process can be applied to gesture analysis (e.g. hand gestures) with all of the analysis being accomplished or augmented by a mobile device, a server, semiconductor-based logic, and so on.

Figure 19:
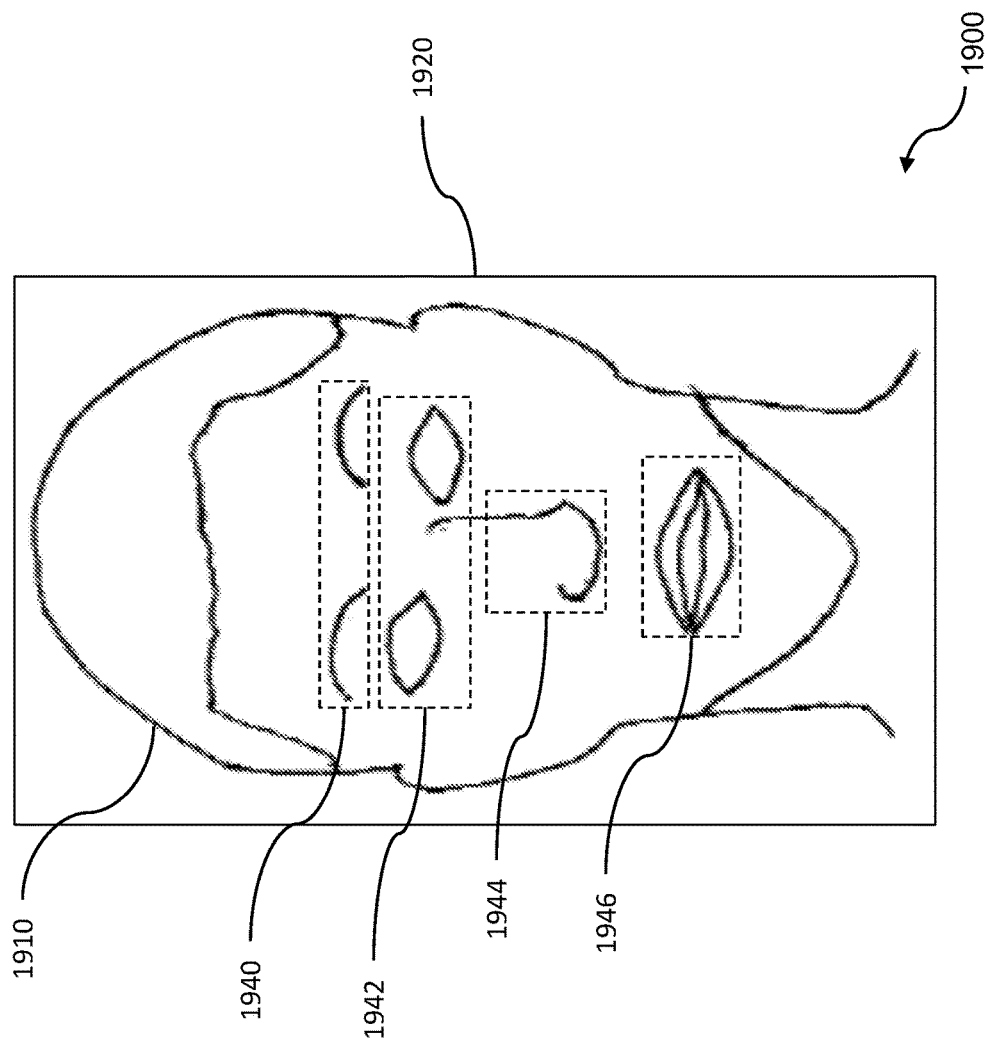
FIG. 19 shows example facial data collection including regions.
Figure 19:
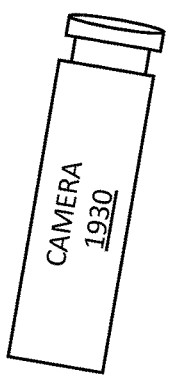

FIG. 19 shows example facial data collection including regions. The collecting of facial data including regions can be performed for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. Facial analysis can be used to determine, predict, estimate, etc. cognitive states, emotions, and so on of a person from whom facial data can be collected. The one or more emotions that can be determined by the analysis can be represented by an image, a figure, an icon, etc. The representative icon can include an emoji. One or more emoji can be used to represent a cognitive state, a mood, etc. of an individual, or to represent food, a geographic location, the weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1900, facial data can be collected, where the facial data can include regions of a face. The facial data that is collected can be based on sub-sectional components of a population. When more than one face can be detected in an image, facial data can be collected for one face, some faces, all faces, and so on. The facial data, which can include facial regions, can be collected using any of a variety of electronic hardware and software techniques. The facial data can be collected using sensors including motion sensors, infrared sensors, physiological sensors, imaging sensors, and so on. A face 1910 can be observed using a camera 1930, a sensor, a combination of cameras and/or sensors, and so on. The camera 1930 can be used to collect facial data that can be used to determine that a face is present in an image. When a face is present in an image, a bounding box 1920 can be placed around the face. Placement of the bounding box around the face can be based on detection of facial landmarks. The camera 1930 can be used to collect from the bounding box 1920 facial data, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1930 relative to the face 1910, the number of cameras and/or sensors used, the illumination of the face, any obstructions to viewing the face, and so on.

The facial regions that can be collected by the camera 1930, sensor, or combination of cameras and/or sensors can include any of a variety of facial features. The facial features that can be included in the facial regions that are collected can include eyebrows 1940, eyes 1942, a nose 1944, a mouth 1946, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1930, sensor, or combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth portion of skin such as a smooth portion of a check. A gradient in a facial region can include values assigned to local skin texture, shading, etc. A gradient can be used to encode, for example, a texture, by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include shape of a face, eyes, nose, mouth, ears, and so on. As with color in a facial region, shape in a facial region can be used to determine demographic data including ethnicity, culture, age, gender, and so on.

The facial regions can be detected based on detection of edges, boundaries, and so on, of features that can be included in an image. The detection can be based on various types of analysis of the image. The features that can be contained in the image can include one or more faces. A boundary can refer to a contour in an image plane where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change, in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis, including, but not limited to, density estimation, support vector machines (SVMs), logistic regression, classification trees, and so on. By way of example, consider facial features that can include the eyebrows 1940. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate that the person from whom the facial data can be collected is annoyed, confused, unhappy, and so on. In another example, consider facial features that can include a mouth 1946. One or more classifiers can be used to analyze the facial region that can include the mouth to determine a probability for either a presence or an absence of mouth edges turned up to form a smile. Multiple classifiers can be used to determine one or more facial expressions.

Figure 20:
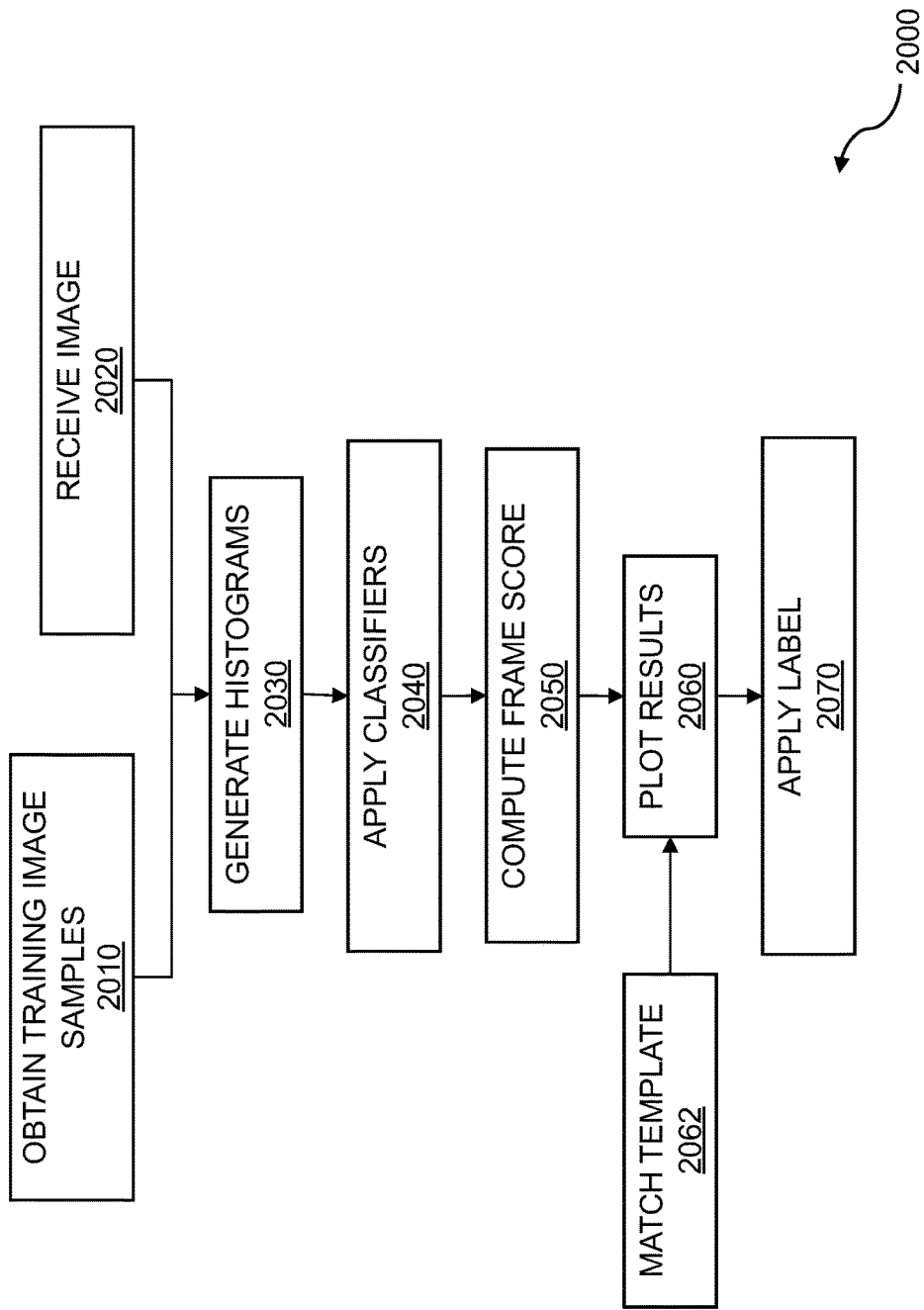
FIG. 20 is a flow diagram for detecting facial expressions.

FIG. 20 is a flow diagram for detecting facial expressions. The detection of facial expressions can be performed for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. The flow 2000, or portions thereof, can be implemented in semiconductor logic, can be accomplished using a mobile device, can be accomplished using a server device, and so on. The flow 2000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AUs), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 2000 begins by obtaining training image samples 2010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 2000 continues with receiving an image 2020. The image 2020 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 2000 continues with generating histograms 2030 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 2000 continues with applying classifiers 2040 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 2000 continues with computing a frame score 2050. The score computed for an image, where the image can be a frame from a video, can be used to determine the presence of a facial expression in the image or video frame. The score can be based on one or more versions of the image 2020 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is implemented can be used to identify symmetrical facial expressions (e.g. smile), asymmetrical facial expressions (e.g. outer brow raiser), and so on.

The flow 2000 continues with plotting results 2060. The results that are plotted can include one or more scores for one or more frames computed over a given time t. For example, the plotted results can include classifier probability results from analysis of HoGs for a sequence of images and video frames. The plotted results can be matched with a template 2062. The template can be temporal and can be represented by a centered box function or another function. A best fit with one or more templates can be found by computing a minimum error. Other best-fit techniques can include polynomial curve fitting, geometric curve fitting, and so on. The flow 2000 continues with applying a label 2070. The label can be used to indicate that a particular facial expression has been detected in the one or more images or video frames which constitute the image 2020 that was received. The label can be used to indicate that any of a range of facial expressions has been detected, including a smile, an asymmetric smile, a frown, and so on. Various steps in the flow 2000 may be changed in order, repeated, omitted, or the like without departing from the disclosed concepts. Various embodiments of the flow 2000 can be included in a computer program product embodied in a non-transitory computer readable medium that includes code executable by one or more processors. Various embodiments of the flow 2000, or portions thereof, can be included on a semiconductor chip and implemented in special purpose logic, programmable logic, and so on.

Figure 21:
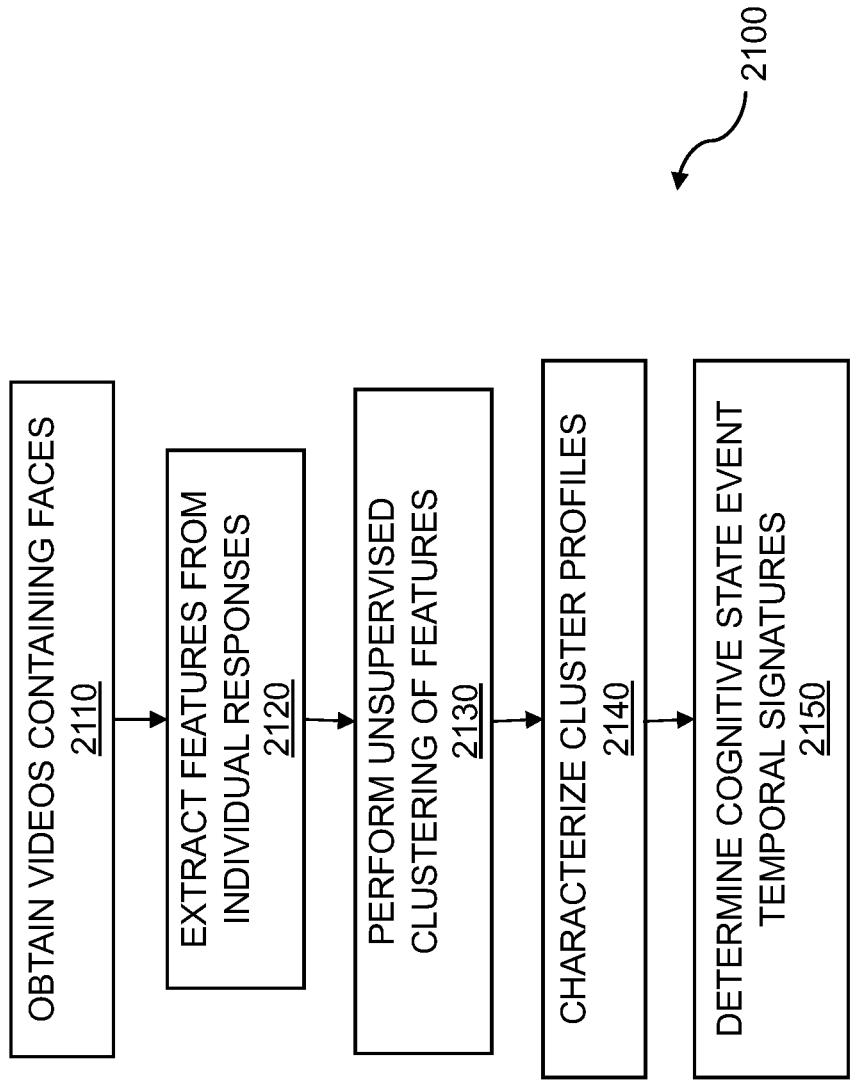
FIG. 21 is a flow diagram for the large-scale clustering of facial events.

FIG. 21 is a flow diagram for the large-scale clustering of facial events. The large-scale clustering of facial events can be performed for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt in to the video data collection. The video event can be a commercial, a political ad, an educational segment, and so on.

The flow 2100 includes obtaining videos containing faces 2110. The videos can be obtained using one or more cameras, where the cameras can include a webcam coupled to one or more devices employed by the one or more people using the web-based framework. The flow 2100 continues with extracting features from the individual responses 2120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 2100 continues with performing unsupervised clustering of features 2130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 2100 includes characterizing cluster profiles 2140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared to various demographic groups, where the groups can be formed based on geographic location, age, ethnicity, gender, and so on.

The flow 2100 can include determining cognitive state event temporal signatures 2150. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 2100 may be changed in order, repeated, omitted, or the like without departing from the disclosed concepts. Various embodiments of the flow 2100 can be included in a computer program product embodied in a non-transitory computer readable medium that includes code executable by one or more processors. Various embodiments of the flow 2100, or portions thereof, can be included on a semiconductor chip and implemented in special purpose logic, programmable logic, and so on.

Figure 22:
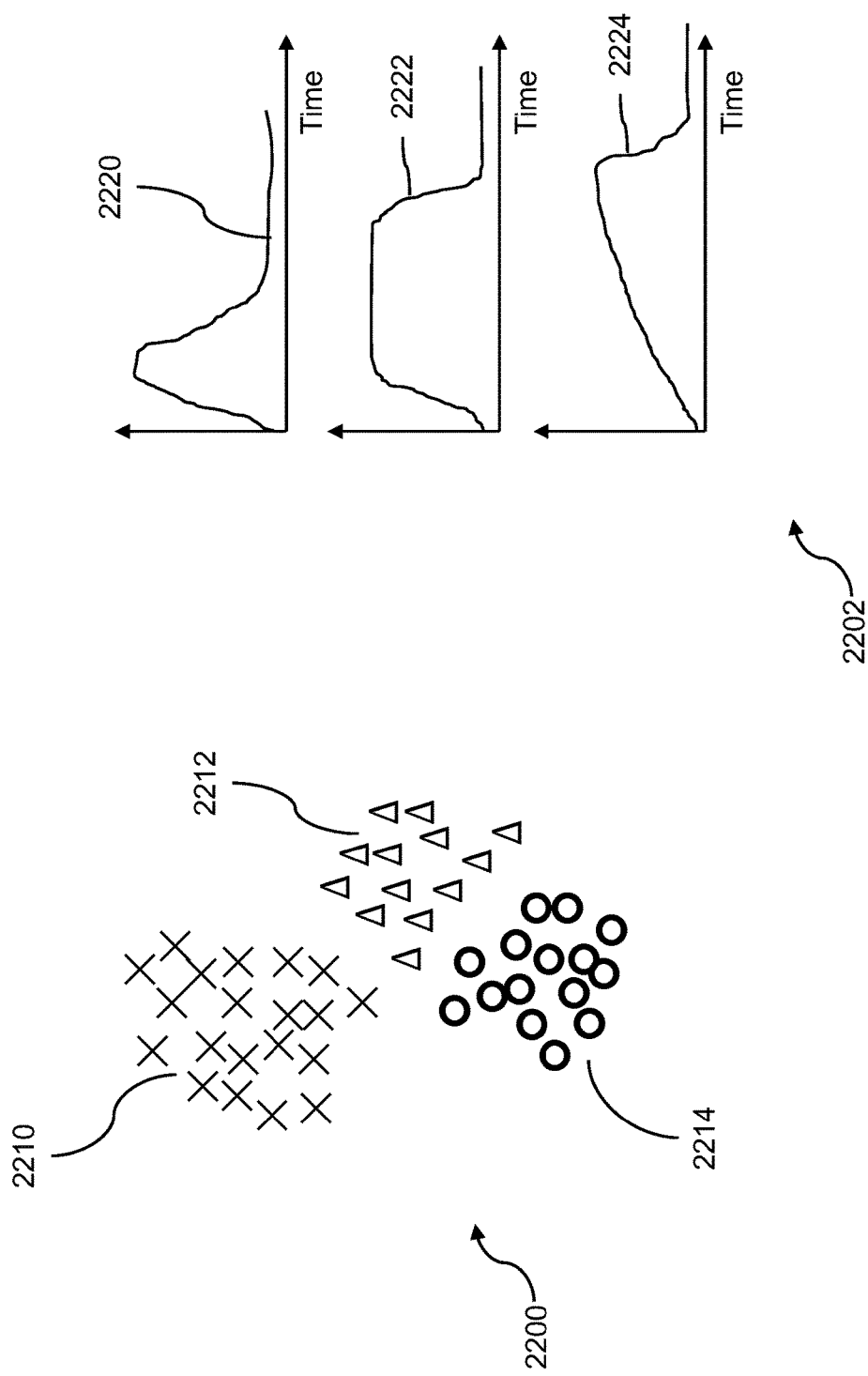
FIG. 22 shows unsupervised clustering of features and characterizations of cluster profiles.

FIG. 22 shows unsupervised clustering of features and characterizations of cluster profiles. The clustering of features and characterizations of cluster profiles can be performed for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. Features including samples of facial data can be clustered using unsupervised clustering. Various clusters can be formed which include similar groupings of facial data observations. The example 2200 shows three clusters, clusters 2210, 2212, and 2214. The clusters can be based on video collected from people who have opted in to video collection. When the collected data is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 2202 can be generated based on the clusters that can be formed from unsupervised clustering, with time shown on the x-axis and intensity or frequency shown on the y-axis. The cluster profiles can be based on captured facial data, including facial expressions. The cluster profile 2220 can be based on the cluster 2210, the cluster profile 2222 can be based on the cluster 2212, and the cluster profile 2224 can be based on the cluster 2214. The cluster profiles 2220, 2222, and 2224 can be based on smiles, smirks, frowns, or any other facial expression. The emotional states of the people who have opted in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 23A:
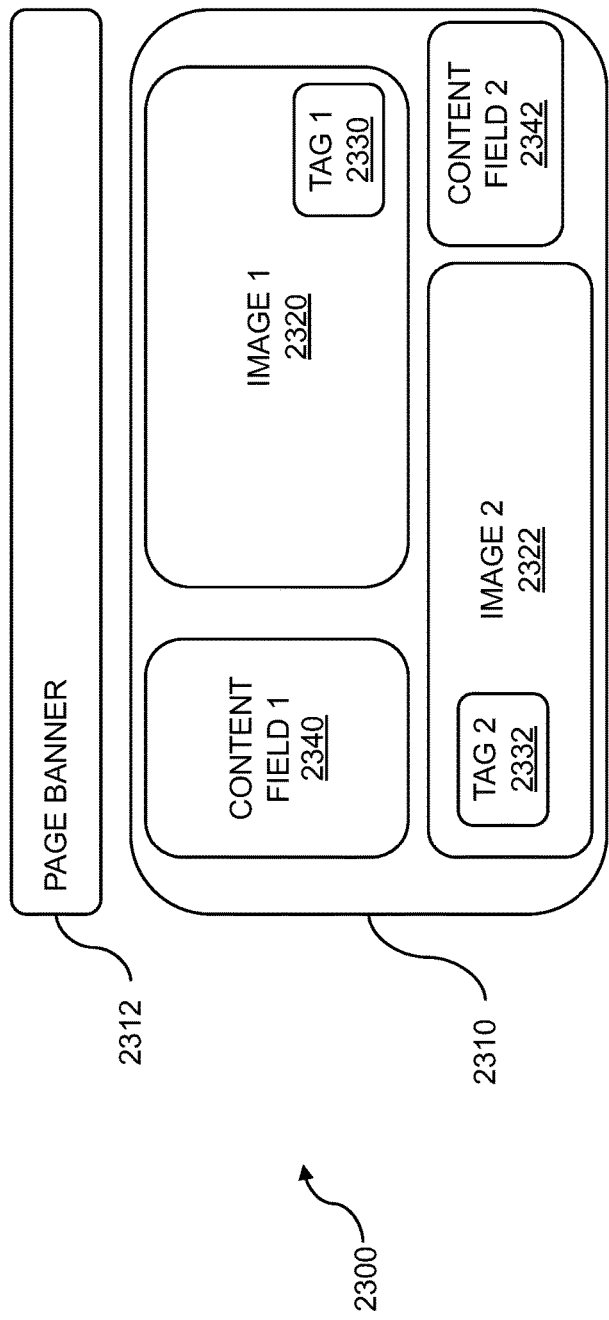
FIG. 23A shows example tags embedded in a webpage.

FIG. 23A shows example tags embedded in a webpage. The tags embedded in the webpage can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people.

Once a tag is detected, a mobile device, a server, semiconductor-based logic, etc. can be used to evaluate associated facial expressions. A webpage 2300 can include a page body 2310, a page banner 2312, and so on. The page body can include one or more objects, where the objects can include text, images, videos, audio, and so on. The example page body 2310 shown includes a first image, image 1 2320; a second image, image 2 2322; a first content field, content field 1 2340; and a second content field, content field 2 2342. In practice, the page body 2310 can contain multiple images and content fields and can include one or more videos, one or more audio presentations, and so on. The page body can include embedded tags, such as tag 1 2330 and tag 2 2332. In the example shown, tag 1 2330 is embedded in image 1 2320, and tag 2 2332 is embedded in image 2 2322. In embodiments, multiple tags are imbedded. Tags can also be embedded in content fields, in videos, in audio presentations, etc. When a user mouses over a tag or clicks on an object associated with a tag, the tag can be invoked. For example, when the user mouses over tag 1 2330, tag 1 2330 can then be invoked. Invoking tag 1 2330 can include enabling a camera coupled to a user's device and capturing one or more images of the user as the user views a media presentation (or digital experience). In a similar manner, when the user mouses over tag 2 2332, tag 2 2332 can be invoked. Invoking tag 2 2332 can also include enabling the camera and capturing images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 23B:
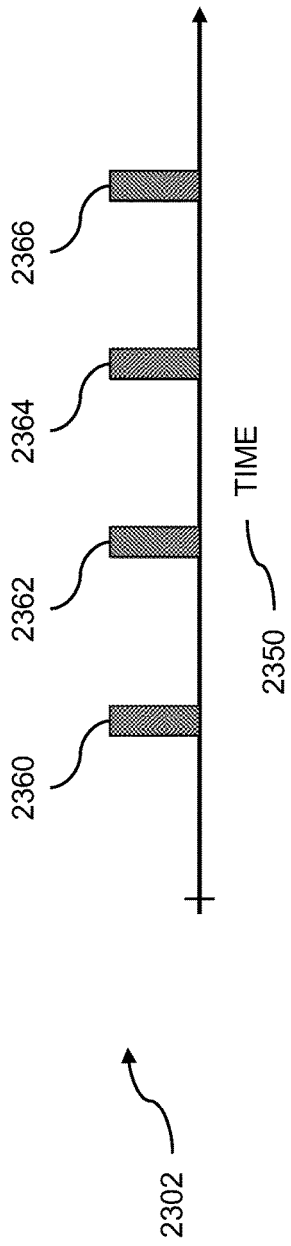
FIG. 23B shows invoking tags to collect images.

FIG. 23B shows invoking tags to collect images. The invoking tags to collect images can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. As previously stated, a media presentation can be a video, a webpage, and so on. A video 2302 can include one or more embedded tags, such as a tag 2360, another tag 2362, a third tag 2364, a fourth tag 2366, and so on. In practice, multiple tags can be included in the media presentation. The one or more tags can be invoked during the media presentation. The collection of the invoked tags can occur over time, as represented by a timeline 2350. When a tag is encountered in the media presentation, the tag can be invoked. When the tag 2360 is encountered, invoking the tag can enable a camera which is coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 2360 does not enable the camera nor does it capture images of the user during the media presentation. The user can indicate an opt-in for certain types of participation, where opting in can be dependent on specific content in the media presentation. The user could opt in to participation in a study of political campaign messages and not opt in for a particular advertisement study. In this case, tags that are related to political campaign messages, advertising messages, social media sharing, etc., and that enable the camera and image capture when invoked, would be embedded in the media presentation social media sharing, and so on. However, tags embedded in the media presentation that are related to advertisements would not enable the camera when invoked. Various other situations of tag invocation are possible.

Figure 24:
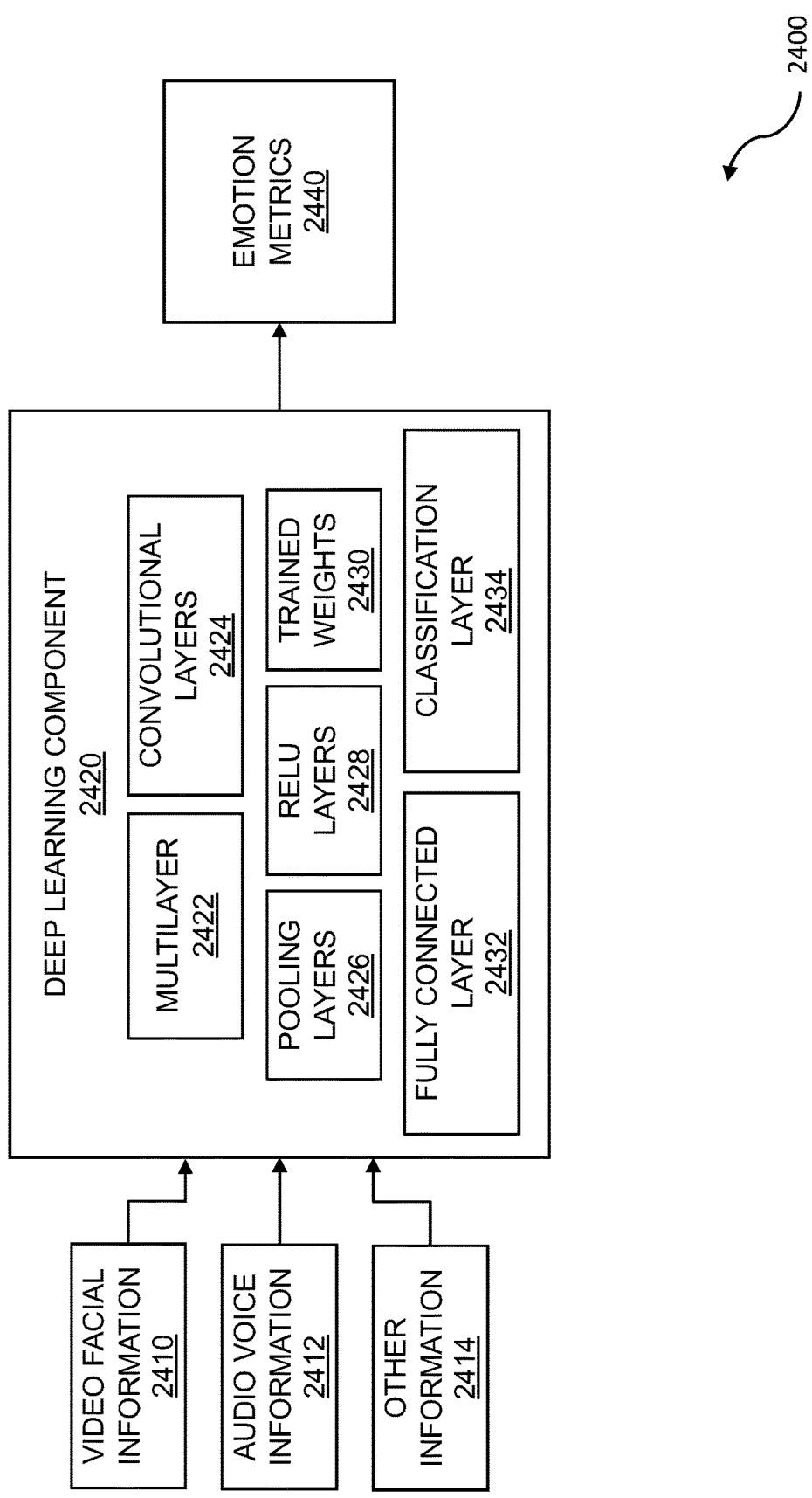
FIG. 24 illustrates a high-level diagram for machine learning/deep learning.

FIG. 24 illustrates a high-level diagram for deep learning. Deep learning, or machine learning, can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people.

Understanding and evaluating moods, emotions, or mental states requires a nuanced evaluation of facial expressions, audio expressions, or other cues generated by people. Mental state analysis is important in many areas such as research, psychology, business, intelligence, law enforcement, and so on. The understanding of mental states can be used in a variety of fields, such as improving marketing analysis, assessing the effectiveness of customer service experiences and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues.

Deep learning is a branch of machine learning which seeks to imitate in software the activity which takes place in layers of neurons in the neocortex of the human brain. Deep learning applications include processing of image data, audio data, and so on. FIG. 24 illustrates a high-level diagram for deep learning 2400. The deep learning can be accomplished using a multilayered convolutional computing system, a convolutional neural network, or other techniques. The deep learning can accomplish image analysis, audio analysis, and other analysis tasks. A deep learning component 2420 collects and analyzes various types of information from a plurality of information channels. The information channels can include video facial information 2410, audio voice information 2412, other information 2414, and so on. In embodiments, the other information can include one or more of electrodermal activity, heart rate, heart rate variability, skin temperature, blood pressure, muscle movements, or respiration.

Returning to the deep learning component 2420, the deep learning component can include a multilayered convolutional computing system 2422. The multilayered convolutional computing system 2422 can include a plurality of layers of varying types. The layers can include one or more convolutional layers 2424 which can be used for learning and analysis. The convolutional layers can include pooling layers 2426 which can combine the outputs of clusters into a single datum. The layers can include one or more Rectified Linear Unit (ReLU) layers 2428. The one or more ReLU layers can implement an activation function such as $f(x)=\max(0,x)$, thus providing an activation with a threshold at zero. The convolutional layers can include trained weights 2430. The trained weights can be based on learning, where the learning uses information collected from one or more individuals via a plurality of information channels. The trained weights can be used to enable the multilayer convolutional computing system to determine image characteristics, voice characteristics, and so on.

The deep learning component 2420 can include a fully connected layer 2432. The fully connected layer 2432 processes each data point from the output of a collection of intermediate layers. The fully connected layer 2432 takes all data points in the previous layer and connects them to every single node contained within the fully connected layer. The output of the fully connected layer 2432 can provide input to a classification layer 2434. The classification layer can be used to classify emotional states, mental states, moods, and so on. The classification can be based on using classifiers. The deep learning component 2420 provides data that includes emotion metrics 2440. The emotion metrics can include an emotion type, a number of occurrences of the emotional type, the intensity of the emotional type, and so on. The emotion metric can be based on a threshold value, on a target value, on a goal, etc. The emotion metric can be based on emotion types that can occur over a period of time. More than one emotion metric can be provided.

Figure 25:
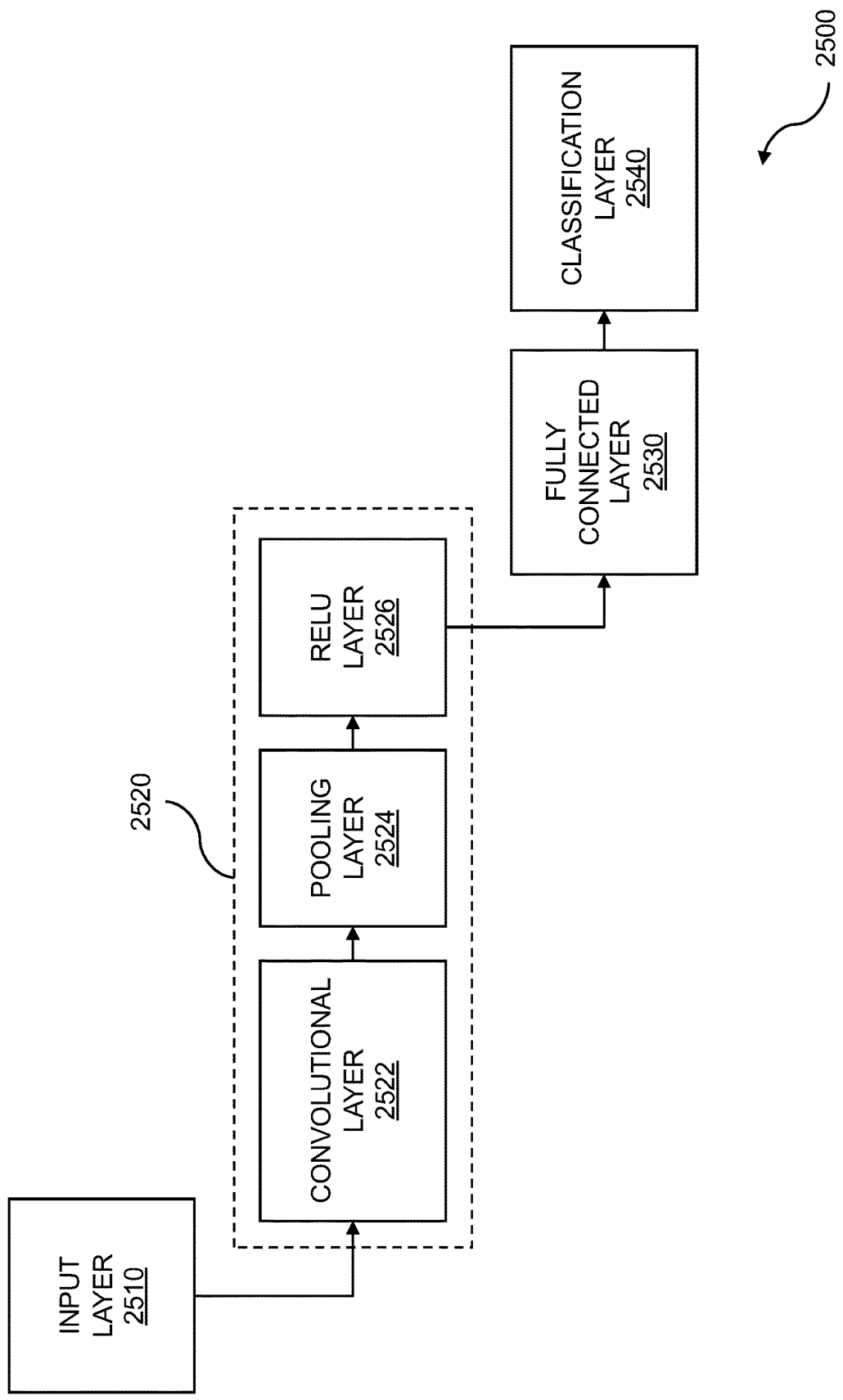
FIG. 25 is an example showing a convolutional neural network.

FIG. 25 is an example showing a convolutional neural network. A convolutional neural network can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people.

Emotion analysis is a very complex task. Understanding and evaluating moods, emotions, or mental states requires a nuanced evaluation of facial expressions or other cues generated by people. Mental state analysis is important in many areas such as research, psychology, business, intelligence, law enforcement, and so on. The understanding of mental states can be used in a variety of fields, such as improving marketing analysis, assessing the effectiveness of customer service experiences and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the mental state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal or control. Thus, by analyzing facial expressions en masse, important information regarding the mental state of the audience can be obtained.

Analysis of facial expressions is also a complex undertaking. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, physiological data, and so on. Facial data as contained in the raw video data can include information on one or more action units such as head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be obtained, where the physiological data can be obtained using a camera or other image capture device, without contacting the person or persons. Respiration, heart rate, heart rate variability, perspiration, temperature, and other physiological indicators of mental state can be determined by analyzing the images and video data.

Analysis of expressions emanating from human audio is also highly complex. Audio data can include speech, grunts, groans, shouts, screams, and so on. Further, the method of how the audio is produced can greatly influence the one or more expressions extracted from the audio. As a result, the audio data, such as voice data, can be evaluated for timbre, prosody, vocal register, vocal resonance, pitch, loudness, speech rate, language content, and so on. The evaluation results can be associated with mental states, emotional states, moods, and so on. For example, loud, rapid, shrill speech can indicate anger, while moderate, controlled speech including polysyllabic words can indicate confidence.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications can include image recognition, facial recognition, etc. Image data applications can include differentiating dogs from cats, identifying different human faces, and the like. The image data applications can include identifying moods, mental states, emotional states, and so on, from the facial expressions of the faces that are identified. Audio data applications can include analyzing audio input such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, volume, speech rate, or language content. The voice data analysis can be used to determine one or more moods, mental states, emotional states, etc.

The artificial neural network which forms the basis for deep learning is based on layers. The layers can include an input layer, a convolutional layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolutional layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of mental state. The last layer of the convolutional neural network can be the final classification layer. The output of the final classification layer can be indicative of mental state of faces within the images that are provided to input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to next layer. Weights adjust the output of one layer as it is fed to the next layer. When the final layer is reached, the output of the final layer can be a facial expression, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning of weights can be accomplished during a feed-forward pass through the multilayered neural network. In a feed-forward arrangement, the information moves forward, from the input nodes, through the hidden nodes and on to the output nodes. Additionally, the weights can be updated during a backpropagation process through the multilayered analysis engine.

Returning to the figure, FIG. 25 illustrates a system diagram 2500 for deep learning. The system for deep learning can be used for multimodal machine learning. The system for deep learning can be accomplished using a convolutional neural network or other techniques. The deep learning can accomplish facial recognition and analysis tasks. The network includes an input layer 2510. The input layer 2510 receives image data. The image data can be input in a variety of formats, such as JPEG, TIFF, BMP, and GIF. Compressed image formats can be decompressed into arrays of pixels, wherein each pixel can include an RGB tuple. The input layer 2510 can then perform processing such as identifying boundaries of the face, identifying landmarks of the face, extracting features of the face, and/or rotating a face within the plurality of images.

The network includes a collection of intermediate layers 2520. The multilayered analysis engine can include a convolutional neural network. Thus, the intermediate layers can include a convolutional layer 2522. The convolutional layer 2522 can include multiple sublayers, including hidden layers within it. The output of the convolutional layer 2522 feeds into a pooling layer 2524. The pooling layer 2524 performs a data reduction, which makes the overall computation more efficient. Thus, the pooling layer reduces the spatial size of the image representation to reduce the number of parameters and computations in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 2524. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (ReLU) layer 2526. The output of the pooling layer 2524 can be input to the ReLU layer 2526. In embodiments, the ReLU layer implements an activation function such as $f(x)-max(0,x)$, thus providing an activation with a threshold at zero. In some embodiments, the ReLU layer 2526 is a leaky ReLU layer. In this case, instead of the activation function providing zero when x<0, a small negative slope is used, resulting in an activation function such as $f(x)=1(x<0)(ax)+1(x>=0)(x)$. This can reduce the risk of "dying ReLU" syndrome, where portions of the network can be "dead" with nodes/neurons that do not activate across the training dataset. The image analysis can comprise training a multilayered analysis engine using the plurality of images, wherein the multilayered analysis engine can comprise multiple layers that include one or more convolutional layers 2522 and one or more hidden layers, and wherein the multilayered analysis engine can be used for emotion analysis.

The example 2500 includes a fully connected layer 2530. The fully connected layer 2530 processes each pixel/data point from the output of the collection of intermediate layers 2520. The fully connected layer 2530 takes all neurons in the previous layer and connects them to every single neuron it has. The output of the fully connected layer 2530 provides input to a classification layer 2540. The output of the classification layer 2540 provides a facial expression and/or mental state as its output. Thus, a multilayered analysis engine such as the one depicted in FIG. 25 processes image data using weights, models the way the human visual cortex performs object recognition and learning, and provides effective analysis of image data to infer facial expressions and mental states.

Figure 26:
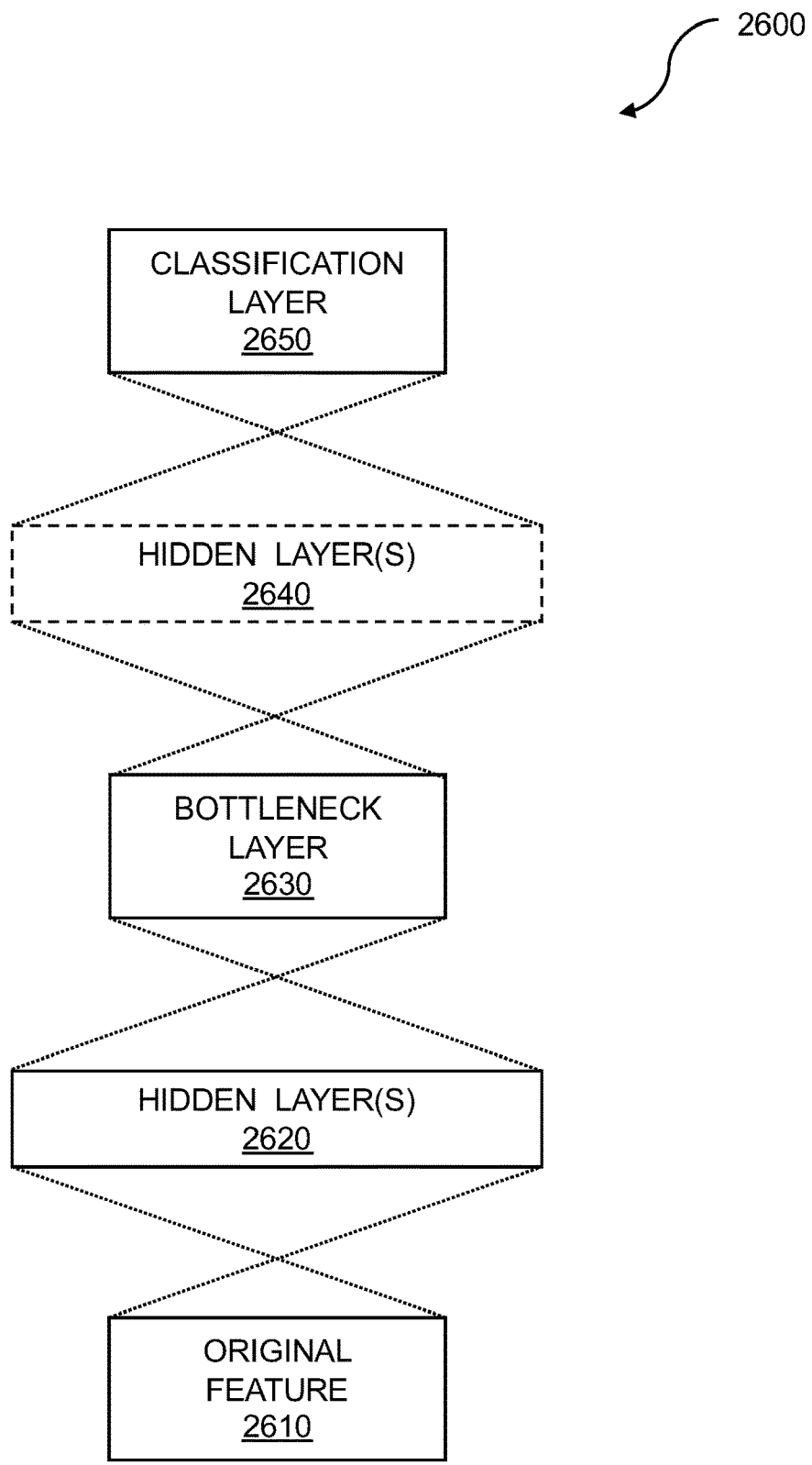
FIG. 26 illustrates a bottleneck layer within a deep learning environment.

FIG. 26 illustrates a bottleneck layer within a deep learning environment. A bottleneck layer can be a layer of a deep neural network and can be used for remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people.

Layers of a deep neural network can include a bottleneck layer 2600. A bottleneck layer can be used for a variety of applications such as facial recognition, voice recognition, emotional state recognition, and so on. The deep neural network in which the bottleneck layer is located can include a plurality of layers. The plurality of layers can include an original feature layer 2610. A feature such as an image feature can include points, edges, objects, boundaries between and among regions, properties, and so on. The deep neural network can include one or more hidden layers 2620. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to an emotional or expressive face or voice. In some cases, individual bottleneck layers can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 2630. The bottleneck layer can include a fewer number of nodes than the one or more preceding hidden layers. The bottleneck layer can create a constriction in the deep neural network or other network. The bottleneck layer can force information that is pertinent to a classification into a low dimensional representation. The bottleneck features can be extracted using an unsupervised technique. In other embodiments, the bottleneck features can be extracted in a supervised manner. The supervised technique can include training the deep neural network with a known dataset. The features can be extracted from an autoencoder such as a variational autoencoder, a generative autoencoder, and so on. The deep neural network can include hidden layers 2640. The number of hidden layers can include zero hidden layers, one hidden layer, a plurality of hidden layers, and so on. The hidden layers following the bottleneck layer can include more nodes than the bottleneck layer. The deep neural network can include a classification layer 2650. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 27:
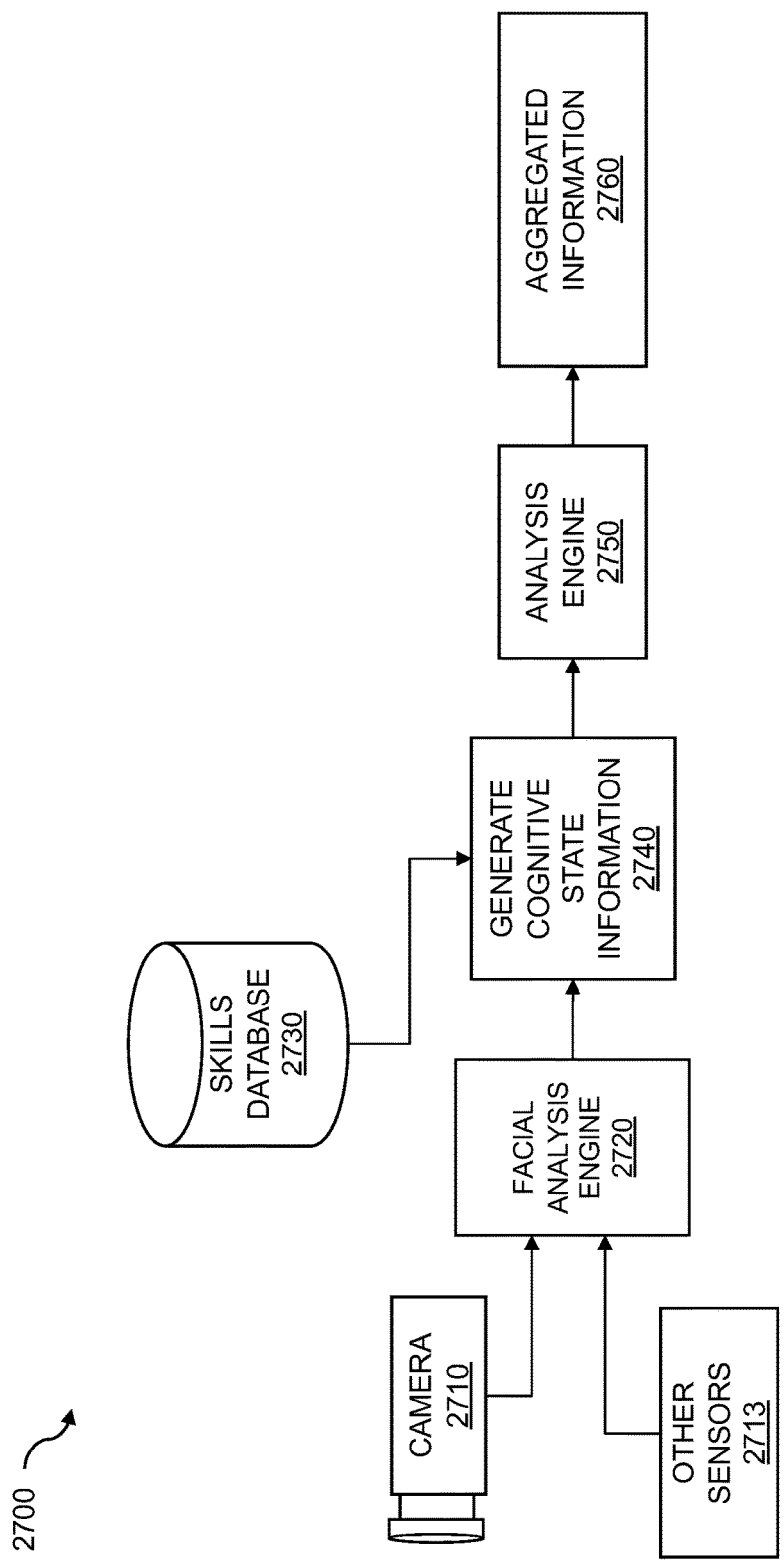
FIG. 27 illustrates a block diagram for image-based file system manipulation.

FIG. 27 illustrates a block diagram for image-based file system manipulation. Image-based file system manipulation can be used to enable remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people.

The block diagram 2700 includes a camera 2710. The camera 2710 can capture an image or a plurality of images. More than one camera can be used. The camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The camera 2710 can be coupled to a facial analysis engine 2720. Other sensors 2713 can also be coupled to the analysis engine to augment facial analysis. The other sensors 2713 could include biosensors which can evaluate electrodermal activity, heart rate, perspiration, respiration, blood sugar, and the like. The facial analysis engine can analyze an image from the plurality of images and can capture cognitive state data, where the cognitive state data can include facial data for the individual. The facial analysis engine 2720 can be implemented using downloaded classifiers running under control of a connection data structure managed by an API. The facial analysis engine 2720 can be coupled to a cognitive state information generator 2740. The cognitive state information generator can generate the cognitive state information for an individual or a plurality of individuals. The cognitive state information generator can augment the facial analysis data from the facial analysis engine 2720. The cognitive state information generator can be implemented on a machine learning system. The facial analysis engine 2720 can calculate a facial expression metric associated with the facial data. The facial expression metric can be further analyzed to generate a cognitive state metric. All or part of the analysis can be performed on a neural network. The neural network can use classifiers to translate facial data into a cognitive state metric. The neural network can be integrated or partitioned over several devices, including a portable device such as a cell phone, a server that is local or remote, or a cloud service, to name just a few. The neural network can be part of a machine learning system. Some embodiments further include calculating a facial expression metric for the individual based on the classifying. Some embodiments further include generating a cognitive state metric for the individual based on the facial expression metric. And some embodiments further include the cognitive state metric in the translating.

Augmented information can be included in the analysis. The augmented information can include a voice, a context such as an environment, the time and date, social information, news cycle information, and so on. The cognitive state information generator can be coupled to a skills database 2730. The skills database 2730 can include filtering information, temporal information, logical information, and so on. The cognitive state information generator can be coupled to an analysis engine 2750. The analysis engine can be based on behavioral models. The analysis engine can provide aggregated cognitive state information 2760. The aggregated information can be used for display on one or more local devices.

Figure 28:
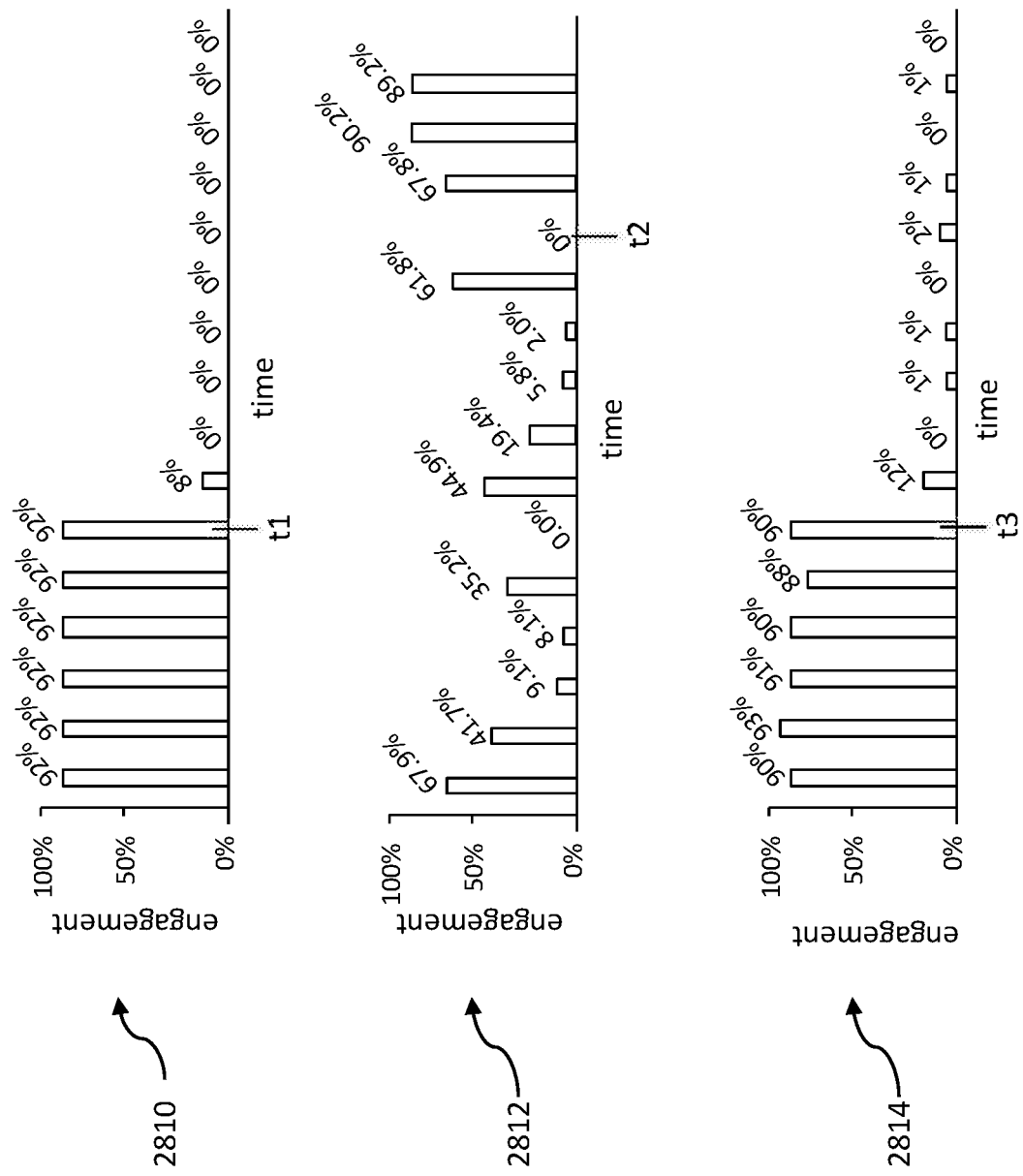
FIG. 28 is an example illustrating facial data that can be used to generate a cognitive state metric.

FIG. 28 is an example illustrating facial data that can be used to generate a cognitive state metric. The cognitive state metric can be used in remote computing analysis for cognitive state data metrics. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people.

FIG. 28 includes three charts, charts 2810, 2812, and 2814. Each chart has a horizontal axis of time, and a vertical axis of an engagement level, which may be derived from cognitive state data. In other embodiments, cognitive state data or other data derived from cognitive state data may be used to generate cognitive state metrics, such as measures of happiness, inattentiveness, concentration, and so on. Each bar on the chart may represent a time window comprising a fixed unit of time, such as one minute. In chart 2810, until time t1, the engagement level is at 92%, indicating that the user is mostly focused on the displayed content. After time t1, the next bar indicates a very low engagement level because at some point during that time window, the user left the area. In the subsequent time windows, the engagement level is zero, as the individual is no longer present.

In chart 2812, the individual remains present in front of the rendered content, but for a portion of the video, he frequently looks away. As can be seen in the chart 2812, up until time t2, the engagement level is sporadic, fluctuating between low and midrange levels. After time t2, the engagement level increases. In such an embodiment where digital media content is modified based on viewership, a chart such as 2812 indicates that the ending of the video is engaging to the individual, while earlier in the video, before time t2, the video was not as engaging. Thus, in embodiments, the modification includes shortening the video by deleting and/or shortening scenes of the video prior to time t2, in order to better hold the individual's attention and interest.

In chart 2814, the individual remains present in front of the rendered content, but for a portion of the video, he is frequently looking away by averting his gaze away from the screen that is presenting the media content. As can be seen in chart 2814, up until time t3, the engagement level is relatively high, indicating a high level of focus by the individual on the media content. After time t3, the engagement level significantly decreases. Each detected engagement level may be considered cognitive state data. In order to generate a cognitive state metric based on a chart such as 2814, the cognitive state data may be processed in any appropriate and desired fashion.

For example, groups of three sequential engagement levels may be averaged to produce cognitive state metrics for a plurality of time periods. As another example, all of the engagement levels for a given time period may be summed and divided by the number of engagement levels that are below 50% in order to determine a cumulative cognitive state metric. In chart 2810, a cumulative cognitive state metric may be determined by summing all of the engagement levels (560) and dividing by the number of engagement levels below 50% (ten), resulting in a cumulative cognitive state metric of 560/10 or 56. For chart 2810, a cumulative cognitive state metric may be determined by summing all of the engagement levels (543.1) and dividing by the number of engagement levels below 50% (ten), resulting in a cumulative cognitive state metric of 543.1/10 or 54.31. For chart 2814, a cumulative cognitive state metric may be determined by summing all of the engagement levels (560) and dividing by the number of engagement levels below 50% (ten in chart 2814), resulting in a cumulative cognitive state metric of 56. Thus, if chart 2810 has a cumulative cognitive state metric of 56, chart 2812 has a metric of 54.31, and chart 2814 has a metric of 56, it may be determined that charts 2810 and 2814 indicate roughly equal levels of engagement while chart 2812 indicates slightly lower engagement than that shown by charts 2810 and 2814. As further examples, if a user is 100% engaged for 8 of 16 sample periods and 49% engaged for the remaining eight sample periods, the cumulative cognitive state metric may be calculated as 100, indicating more engagement than is shown in charts 2810, 2812, and 2814. However, if a user is only 80% engaged for 4 of 16 sample periods and 0% engaged for the remaining twelve sample periods, the cumulative cognitive state metric may be calculated as 26.67, indicating less engagement than is shown in charts 2810, 2812, and 2814. Although only a selection of cognitive state metrics is explicitly discussed herein, it will be understood after reviewing this application in its entirety that any number of different cognitive state metrics may be used.

Figure 29:
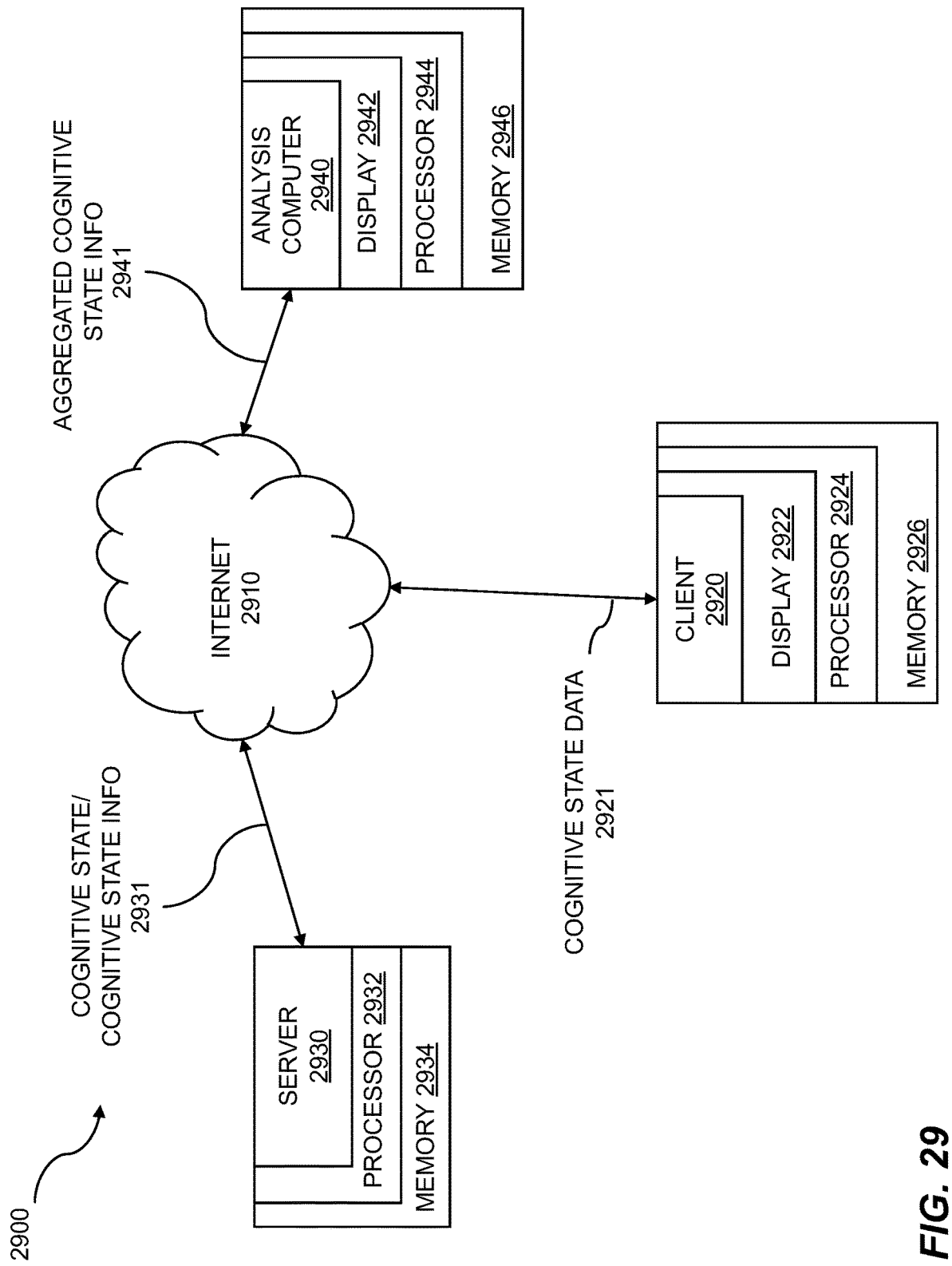
FIG. 29 is a diagram of a system for remote computing analysis for cognitive state metrics.

FIG. 29 is a diagram of a system 2900 for remote computing analysis for cognitive state metrics. Remote computing analysis for cognitive state data metrics is performed. Cognitive state data from a plurality of people is collected as they interact with a rendering. The cognitive state data includes video facial data collected on one or more local devices from the plurality of people. Information is uploaded to a remote server. The information includes the cognitive state data. A facial expression metric based on a plurality of image classifiers is calculated for each individual within the plurality of people. Cognitive state information is generated for each individual, based on the facial expression metric for each individual. The cognitive state information for each individual within the plurality of people who interacted with the rendering is aggregated. The aggregation is based on the facial expression metric for each individual. The cognitive state information that was aggregated is displayed on at least one of the one or more local devices.

Image analysis can be performed for data collected from a remote computing device. The image analysis can be used for people as they interact with the Internet. The Internet 2910, intranet, or another computer network can be used for communication between the various computers. A client computer 2920 has a memory 2926 which stores instructions and one or more processors 2924 coupled to the memory 2926, wherein the one or more processors 2924 can execute instructions. The client computer 2920 can also have an internet connection to carry cognitive state data 2921 and a display 2922 that can present various renderings to a user. The client computer 2920 can collect cognitive state data from a plurality of people as they interact with a rendering. In some embodiments, there are multiple client computers 2920 that each collect cognitive state data from one person or a plurality of people as they interact with a rendering. In other embodiments, the client computer 2920 receives cognitive state data collected from a plurality of people as they interact with a rendering. Once the cognitive state data has been collected, the client computer can upload information to a server 2930, based on the cognitive state data from the plurality of people who interact with the rendering. The client computer 2920 can communicate with the server 2930 over the internet 2910, some other computer network, or by another method suitable for communication between two computers. In some embodiments, the server 2930 functionality is embodied in the client computer.

The server 2930 can have an internet connection for cognitive states or cognitive state information 2931, a memory 2934 which stores instructions, and one or more processors 2932 coupled to the memory 2934, wherein the one or more processors 2932 can execute instructions. The server 2930 can receive cognitive state information collected from a plurality of people as they interact with a rendering from the client computer 2920, and can aggregate cognitive state information on the plurality of people who interact with the rendering. The server 2930 can also associate the aggregated cognitive state information with the rendering and with the collection of norms for the context being measured. In some embodiments, the server 2930 also allows a user to view and evaluate the cognitive state information that is associated with the rendering, but in other embodiments, an analysis computer 2940 requests the aggregated cognitive state information 2941 from the server 2930. The server 2930 can then provide the aggregated cognitive state information 2941 to a requester, the analysis computer 2940. In some embodiments, the client computer 2920 also functions as the analysis computer 2940.

The analysis computer 2940 can have a memory 2946 which stores instructions, and one or more processors 2944 coupled to the memory 2946, wherein the one or more processors 2944 can execute instructions. The analysis computer can use its internet, or another computer communication method, to request the aggregated cognitive state information 2941 from the server. The analysis computer 2940 can receive aggregated cognitive state information 2941, based on the cognitive state data, from the plurality of people who interact with the rendering and can present the aggregated cognitive state information with the rendering on a display 2942. In some embodiments, the analysis computer is set up for receiving cognitive state data collected from a plurality of people as they interact with a rendering, in a real-time or near real-time embodiment. In at least one embodiment, a single computer incorporates the client, server, and analysis functionality.

The system 2900 can implement a system for analysis comprising: a memory which stores instructions; one or more processors coupled to the memory wherein the one or more processors, when executing the instructions which are stored, are configured to: collect cognitive state data from a plurality of people as they interact with a rendering, wherein the cognitive state data includes video facial data, collected on one or more local devices, from the plurality of people; upload information to a remote server, wherein the information includes the cognitive state data; calculate a facial expression metric, based on a plurality of image classifiers, for each individual within the plurality of people; generate cognitive state information for each individual, based on the facial expression metric for each individual; aggregate the cognitive state information for each individual within the plurality of people who interacted with the rendering, based on facial expression metric for each individual; and display the cognitive state information that was aggregated, with the rendering, on at least one of the one or more local devices.

The system 2900 can enable a computer program product embodied in a non-transitory computer readable medium for analysis, the computer program product comprising code which causes one or more processors to perform operations of: collecting cognitive state data from a plurality of people as they interact with a rendering, wherein the cognitive state data includes video facial data, collected on one or more local devices, from the plurality of people; uploading information to a remote server, wherein the information includes the cognitive state data; calculating a facial expression metric, based on a plurality of image classifiers, for each individual within the plurality of people; generating cognitive state information for each individual, based on the facial expression metric for each individual; aggregating the cognitive state information for each individual within the plurality of people who interacted with the rendering, based on facial expression metric for each individual; and displaying the cognitive state information that was aggregated, with the rendering, on at least one of the one or more local devices.

Each of the above methods may be executed on one or more processors on one or more computer systems. Embodiments may include various forms of distributed computing, client/server computing, and cloud-based computing. Further, it will be understood that for each flowchart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, by a computer system, and so on. Any and all of which implementations may be generally referred to herein as a "circuit," "module," or "system."

A programmable apparatus that executes any of the above-mentioned computer program products or computer implemented methods may include one or more processors, microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM), Flash, MRAM, FeRAM, phase change memory, an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for analysis comprising:
    collecting cognitive state data from a plurality of people as they interact with a rendering, wherein the cognitive state data includes video facial data, collected on one or more local devices, from the plurality of people;
    uploading information to a remote server, wherein the information includes the cognitive state data;
    calculating a facial expression metric, based on a plurality of image classifiers, for each individual within the plurality of people;
    generating cognitive state information for each individual, based on the facial expression metric for each individual;
    aggregating the cognitive state information for each individual within the plurality of people who interacted with the rendering, based on the facial expression metric for each individual; and
    displaying, with the rendering, the cognitive state information that was aggregated, on at least one of the one or more local devices, wherein the displaying includes an avatar visualization of the aggregated cognitive state information, wherein the visualization is based on an average of the cognitive state data collected from the plurality of people.

2. The method of claim 1 wherein the cognitive state information includes a cognitive state metric.

3. The method of claim 1 wherein the aggregated cognitive state information includes aggregated cognitive state metrics.

4. The method of claim 3 further comprising deriving norms for the plurality of people.

5. The method of claim 4 wherein the norms for the plurality of people are based on the aggregated cognitive state information.

6. The method of claim 4 wherein the norms for the plurality of people are based on contextual information.

7. The method of claim 4 wherein the norms are derived based on cognitive state event temporal signatures.

8. The method of claim 1 further comprising collecting further cognitive state data from a first individual and comparing the further cognitive state data from the first individual with the aggregated cognitive state information.

9. The method of claim 1 further comprising associating the cognitive state information that was aggregated with the rendering.

10. The method of claim 1 further comprising synchronizing the aggregated cognitive state information with the rendering.

11. The method of claim 1 further comprising capturing contextual information about the rendering.

12. The method of claim 11 wherein the contextual information includes a timeline, a progression of webpages, or an actigraph.

13. The method of claim 1 further comprising inferring cognitive states based on the cognitive state data collected from the plurality of people.

14. The method of claim 1 wherein the calculating includes using an image classifier from a plurality of image classifiers to detect one or more faces in the facial data.

15. The method of claim 1 further comprising tracking eyes to identify the rendering with which interacting is accomplished.

16. The method of claim 15 wherein the tracking of the eyes identifies a portion of the rendering on which the eyes are focused.

17. The method of claim 16 further comprising recording of eye dwell time on the rendering and associating information on the eye dwell time to the rendering and to the cognitive state data.

18. The method of claim 1 wherein aggregation of the cognitive state information is performed on a demographic basis so that cognitive state information is grouped based on the demographic basis.

19. The method of claim 1 wherein the cognitive state information includes two or more cognitive state metrics for an individual within the plurality of people.

20. The method of claim 19 wherein the aggregating further comprises aggregating the two or more cognitive state metrics for the individual with two or more cognitive state metrics for an additional individual within the plurality of people.

21. The method of claim 20 wherein the aggregating is further based on a comparison of matched cognitive state metrics for the individual and the additional individual.

22. The method of claim 1 further comprising creating a visual representation of one or more of the aggregated cognitive state information and cognitive state information on an individual from the plurality of people.

23. The method of claim 22 wherein the visual representation displays the aggregated cognitive state information on a demographic basis, wherein the demographic basis includes at least one of age, ethnicity, and gender.

24. A computer program product embodied in a non-transitory computer readable medium for analysis, the computer program product comprising code which causes one or more processors to perform operations of:
   collecting cognitive state data from a plurality of people as they interact with a rendering, wherein the cognitive state data includes video facial data, collected on one or more local devices, from the plurality of people;
   uploading information to a remote server, wherein the information includes the cognitive state data;
   calculating a facial expression metric, based on a plurality of image classifiers, for each individual within the plurality of people;
   generating cognitive state information for each individual, based on the facial expression metric for each individual;
   aggregating the cognitive state information for each individual within the plurality of people who interacted with the rendering, based on facial expression metric for each individual; and
   displaying the cognitive state information that was aggregated, with the rendering, on at least one of the one or more local devices, wherein the displaying includes an avatar visualization of the aggregated cognitive state information, wherein the visualization is based on an average of the cognitive state data collected from the plurality of people.

25. A system for analysis comprising:
   a memory which stores instructions;
   one or more processors attached to the memory wherein the one or more processors, when executing the instructions which are stored, are configured to:
      collect cognitive state data from a plurality of people as they interact with a rendering, wherein the cognitive state data includes video facial data, collected on one or more local devices, from the plurality of people;
      upload information to a remote server, wherein the information includes the cognitive state data;
      calculate a facial expression metric, based on a plurality of image classifiers, for each individual within the plurality of people;
      generate cognitive state information for each individual, based on the facial expression metric for each individual;
      aggregate the cognitive state information for each individual within the plurality of people who interacted with the rendering, based on facial expression metric for each individual; and
      display the cognitive state information that was aggregated, with the rendering, on at least one of the one or more local devices, wherein displaying includes an avatar visualization of the aggregated cognitive state information, wherein the visualization is based on an average of the cognitive state data collected from the plurality of people.

* * * * *